US011564416B2

(12) United States Patent
Hourmand et al.

(10) Patent No.: US 11,564,416 B2
(45) Date of Patent: *Jan. 31, 2023

(54) NON-NICOTINE POD ASSEMBLIES AND NON-NICOTINE E-VAPING DEVICES

(71) Applicant: Altria Client Services LLC, Richmond, VA (US)

(72) Inventors: Yannick Hourmand, Richmond, VA (US); Christopher Newcomb, Richmond, VA (US); Raymond W. Lau, Richmond, VA (US); Eric Hawes, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 366 days.

This patent is subject to a terminal disclaimer.

(21) Appl. No.: 16/695,563

(22) Filed: Nov. 26, 2019

(65) Prior Publication Data

US 2021/0153566 A1    May 27, 2021

(51) Int. Cl.
    *A24F 40/42*     (2020.01)
    *A61M 11/04*     (2006.01)

(52) U.S. Cl.
    CPC .............. *A24F 40/42* (2020.01); *A61M 11/04* (2013.01)

(58) Field of Classification Search
None
See application file for complete search history.

(56) References Cited

U.S. PATENT DOCUMENTS

| 5,301,666 | A | 4/1994 | Lerk et al. |
| 6,810,883 | B2 | 11/2004 | Felter et al. |
| D552,232 | S | 10/2007 | Collins et al. |
| 7,350,720 | B2 | 4/2008 | Jaworski et al. |
| 7,987,856 | B2 | 8/2011 | Gedevanishvili et al. |
| 8,291,898 | B2 | 10/2012 | Southby et al. |
| 8,424,540 | B2 | 4/2013 | Olegario et al. |
| 8,733,346 | B2 | 5/2014 | Rinker |
| 9,320,301 | B2 | 4/2016 | Memari et al. |

(Continued)

FOREIGN PATENT DOCUMENTS

| CN | 203646511 U | 6/2014 |
| CN | 203828084 U | 9/2014 |

(Continued)

OTHER PUBLICATIONS

Office Action for U.S. Appl. No. 16/695,692 dated Sep. 22, 2021.

(Continued)

*Primary Examiner* — James Harvey
(74) *Attorney, Agent, or Firm* — Harness, Dickey & Pierce, P.L.C.

(57) ABSTRACT

A non-nicotine e-vaping device may include a non-nicotine pod assembly and a device body defining a through hole configured to receive the non-nicotine pod assembly. The non-nicotine pod assembly is configured to hold a non-nicotine pre-vapor formulation. The through hole of the device body includes at least one sidewall that is configured to deflect during an insertion of the non-nicotine pod assembly. One or more sidewalls of the through hole may include at least one protrusion configured to engage with corresponding recesses of the non-nicotine pod assembly so as to retain the non-nicotine pod assembly within the through hole of the device body.

23 Claims, 19 Drawing Sheets

(56) References Cited

U.S. PATENT DOCUMENTS

| | | | |
|---|---|---|---|
| 9,532,604 | B2 | 1/2017 | Conley et al. |
| 9,668,523 | B2 | 6/2017 | Tucker et al. |
| 9,750,284 | B2 | 9/2017 | Rado |
| 9,999,258 | B2 | 6/2018 | Newcomb et al. |
| 10,104,913 | B2 | 10/2018 | Lau et al. |
| 11,123,501 | B2 | 9/2021 | Nettenstrom |
| 2009/0241949 | A1 | 10/2009 | Smutney et al. |
| 2012/0199663 | A1 | 8/2012 | Qiu |
| 2014/0123989 | A1 | 5/2014 | LaMothe |
| 2014/0261487 | A1 | 9/2014 | Chapman et al. |
| 2015/0027457 | A1 | 1/2015 | Janardhan et al. |
| 2015/0101625 | A1 | 4/2015 | Newton et al. |
| 2015/0128971 | A1 | 5/2015 | Verleur et al. |
| 2015/0189919 | A1 | 7/2015 | Liu |
| 2015/0208729 | A1 | 7/2015 | Monsees et al. |
| 2015/0342255 | A1 | 12/2015 | Wu |
| 2015/0342258 | A1 | 12/2015 | Chen |
| 2015/0351456 | A1 | 12/2015 | Johnson et al. |
| 2015/0374039 | A1 | 12/2015 | Zhu |
| 2016/0021933 | A1 | 1/2016 | Thorens et al. |
| 2016/0050975 | A1 | 2/2016 | Worm et al. |
| 2016/0120226 | A1 | 5/2016 | Rado |
| 2016/0309787 | A1 | 10/2016 | Hawes et al. |
| 2016/0309788 | A1 | 10/2016 | Hawes et al. |
| 2016/0309789 | A1 | 10/2016 | Thomas, Jr. |
| 2016/0324216 | A1 | 11/2016 | Li et al. |
| 2016/0345626 | A1 | 12/2016 | Wong et al. |
| 2016/0360789 | A1 | 12/2016 | Hawes et al. |
| 2016/0374399 | A1 | 12/2016 | Monsees et al. |
| 2017/0027227 | A1 | 2/2017 | Lipowicz |
| 2017/0035115 | A1 | 2/2017 | Monsees et al. |
| 2017/0042246 | A1 | 2/2017 | Lau et al. |
| 2017/0071249 | A1 | 3/2017 | Ampolini et al. |
| 2017/0071253 | A1 | 3/2017 | Revell |
| 2017/0095624 | A1 | 4/2017 | Davidson et al. |
| 2017/0135409 | A1 | 5/2017 | Cameron |
| 2017/0150753 | A1 | 6/2017 | Macko |
| 2017/0172209 | A1 | 6/2017 | Saydar et al. |
| 2017/0197044 | A1 | 7/2017 | Buchberger |
| 2017/0202265 | A1 | 7/2017 | Hawes et al. |
| 2017/0231281 | A1 | 8/2017 | Hatton et al. |
| 2017/0231282 | A1 | 8/2017 | Bowen et al. |
| 2017/0258134 | A1 | 9/2017 | Kane |
| 2018/0027879 | A1 | 2/2018 | Gavrielov et al. |
| 2018/0104214 | A1 | 4/2018 | Raichman |
| 2019/0099562 | A1* | 4/2019 | Nettenstrom ..... A61M 15/0021 |
| 2019/0104763 | A1 | 4/2019 | Tucker et al. |
| 2019/0104764 | A1 | 4/2019 | Tucker et al. |
| 2019/0142071 | A1 | 5/2019 | Seok |
| 2019/0166913 | A1 | 6/2019 | Trzecieski |
| 2019/0208820 | A1 | 7/2019 | Reevell |
| 2019/0254345 | A1 | 8/2019 | Hepworth et al. |
| 2019/0274362 | A1 | 9/2019 | Newcomb et al. |
| 2019/0335813 | A1 | 11/2019 | Qiu |
| 2020/0114095 | A1 | 4/2020 | Holroyd et al. |
| 2020/0376210 | A1* | 12/2020 | Simpson ........... A61M 15/0065 |
| 2020/0397046 | A1* | 12/2020 | Lin .................... A24F 40/30 |
| 2021/0068458 | A1 | 3/2021 | Lomas et al. |
| 2021/0153548 | A1 | 5/2021 | Twite et al. |
| 2021/0153549 | A1 | 5/2021 | Twite et al. |
| 2021/0153566 | A1 | 5/2021 | Hourmand et al. |
| 2021/0153567 | A1 | 5/2021 | Twite et al. |
| 2021/0153568 | A1 | 5/2021 | Twite et al. |
| 2021/0153569 | A1 | 5/2021 | Twite et al. |
| 2021/0268215 | A1* | 9/2021 | Israel ................ A61M 15/0003 |
| 2022/0142257 | A1 | 5/2022 | Austin et al. |

FOREIGN PATENT DOCUMENTS

| | | |
|---|---|---|
| CN | 108741232 A | 11/2018 |
| CN | 208692313 U | 4/2019 |
| EP | 3560360 A1 | 10/2019 |
| EP | 3569073 A1 | 11/2019 |
| WO | WO-2016/079152 A1 | 5/2016 |
| WO | WO-2016/096780 A1 | 6/2016 |
| WO | WO-2016/172023 A1 | 10/2016 |
| WO | WO-2016/172802 A1 | 11/2016 |
| WO | WO-2017/102969 A1 | 6/2017 |
| WO | WO-2017/153597 A1 | 9/2017 |
| WO | WO-2017/163045 A1 | 9/2017 |
| WO | WO-2017/163052 A1 | 9/2017 |
| WO | WO-2017/207443 A1 | 12/2017 |
| WO | WO-2018/125674 A1 | 7/2018 |
| WO | WO-2018217440 A1 | 11/2018 |
| WO | WO-2020/039177 A1 | 2/2020 |
| WO | WO-2020/039179 A1 | 2/2020 |

OTHER PUBLICATIONS

Notice of Allowance for U.S. Appl. No. 16/696,007 dated Mar. 7, 2022.
International Search Report and Written Opinion for PCT/US2020/045590 dated Dec. 14, 2020.
International Search Report and Written Opinion for PCT/US2020/045691 dated Jan. 12, 2021.
Invitation to Pay Additional Fees for PCT/EP2020/083536 dated Mar. 1, 2021.
Invitation to Pay Additional Fees for PCT/EP2020/083539 dated Mar. 2, 2021.
Invitation to Pay Additional Fees for PCT/EP2020/083551 dated Mar. 2, 2021.
Invitation to Pay Additional Fees for PCT/EP2020/083549 dated Mar. 2, 2021.
Notice of Allowance for U.S. Appl. No. 16/695,643 dated Dec. 20, 2021.
Notice of Allowance for U.S. Appl. No. 16/695,692 dated Jan. 4, 2022.
Office Action for U.S. Appl. No. 16/696,189 dated Oct. 14, 2021.
Written Opinion for PCT/EP2020/083549 dated Oct. 15, 2021.
Written Opinion for PCT/EP2020/083536 dated Oct. 12, 2021.
Written Opinion for PCT/EP2020/083539 dated Oct. 14, 2021.
Office Action for U.S. Appl. No. 16/695,643 dated Sep. 1, 2021.
Notice of Allowance for U.S. Appl. No. 16/696,007 dated Jan. 28, 2022.
Notice of Allowance for U.S. Appl. No. 16/695,515 dated Feb. 1, 2022.
Office action dated Nov. 10, 2021, issued in corresponding U.S. Appl. No. 16/696,081.
Written Opinion for corresponding International application No. PCT/EP2020/083551 dated Nov. 19, 2021.
International Search Report and Written Opinion for PCT/US2020/045692 dated Nov. 12, 2020.
Notice of Allowance for U.S. Appl. No. 16/696,081 dated Mar. 15, 2022.
Invitation to Pay Fees for PCT/EP2020/083551 dated Oct. 14, 2021.
International Search Report and Written Opinion for corresponding International application No. PCT/EP2020/083536 dated Jun. 11, 2021.
International Search Report and Written Opinion for corresponding International application No. PCT/EP2020/083549 dated Jun. 11, 2021.
International Search Report and Written Opinion for corresponding International application No. PCT/EP2020/083539 dated Jun. 11, 2021.
International Search Report and Written Opinion for PCT/US2020/045588 dated Feb. 2, 2021.
International Search Report and Written Opinion for corresponding International application No. PCT/EP2020/083551 dated Jun. 11, 2021.
Office Action for U.S. Appl. No. 16/696,007 dated Nov. 3, 2021.
Office Action for U.S. Appl. No. 16/696,189 dated Jan. 10, 2022.
Office Action for U.S. Appl. No. 16/695,515 dated Jul. 28, 2021.
Notice of Allowance for U.S. Appl. No. 16/696,189 dated Mar. 28, 2022.
International Preliminary Report on Patentability for PCT/EP2020/083539 dated Feb. 24, 2022.
International Preliminary Report on Patentability for PCT/EP2020/083551 dated Feb. 24, 2022.

(56) References Cited

OTHER PUBLICATIONS

International Preliminary Report on Patentability for PCT/EP2020/083549 dated Feb. 24, 2022.
Office Action for U.S. Appl. No. 16/695,415 dated Mar. 29, 2022.
Office Action for U.S. Appl. No. 16/695,515 dated May 27, 2022.
International Preliminary Report on Patentability for PCT/US2020/045590 dated Jun. 9, 2022.
International Preliminary Report on Patentability for PCT/US2020/045692 dated Jun. 9, 2022.
International Preliminary Report on Patentability for PCT/US2020/045588 dated Jun. 9, 2022.
International Preliminary Report on Patentability for PCT/US2020/045691 dated Jun. 9, 2022.
Office Action for U.S. Appl. No. 16/695,643 dated Apr. 22, 2022.
Notice of Allowance for U.S. Appl. No. 16/695,692 dated Apr. 25, 2022.
Notice of Allowance for U.S. Appl. No. 16/696,007 dated Apr. 28, 2022.
Notice of Allowance for U.S. Appl. No. 16/696,189 dated May 5, 2022.
Notice of Allowance for U.S. Appl. No. 16/696,081 dated May 4, 2022.
Notice of Allowance for corresponding U.S. Appl. No. 16/695,692 dated Jul. 13, 2022.
Notice of Allowance for U.S. Appl. No. 16/696,007 dated Jul. 18, 2022.
Notice of Allowance for U.S. Appl. No. 16/696,189 dated Mar. 10, 2022.
Notice of Allowance for U.S. Appl. No. 16/695,692 dated Mar. 21, 2022.
International Preliminary Report on Patentability for PCT/EP2020/083536 dated Feb. 23, 2022.
Notice of Allowance for U.S. Appl. No. 16/695,643 dated Mar. 24, 2022.
Notice of Allowance for U.S. Appl. No. 16/696,189 dated Jul. 27, 2022.
Notice of Allowance for U.S. Appl. No. 16/695,415 dated Jul. 25, 2022.
Notice of Allowance for U.S. Appl. No. 16/696,081 dated Jul. 29, 2022.
Notice of Allowance dated Oct. 25, 2022 issued in corresponding U.S. Appl. No. 16/695,643.

* cited by examiner

FIG. 1
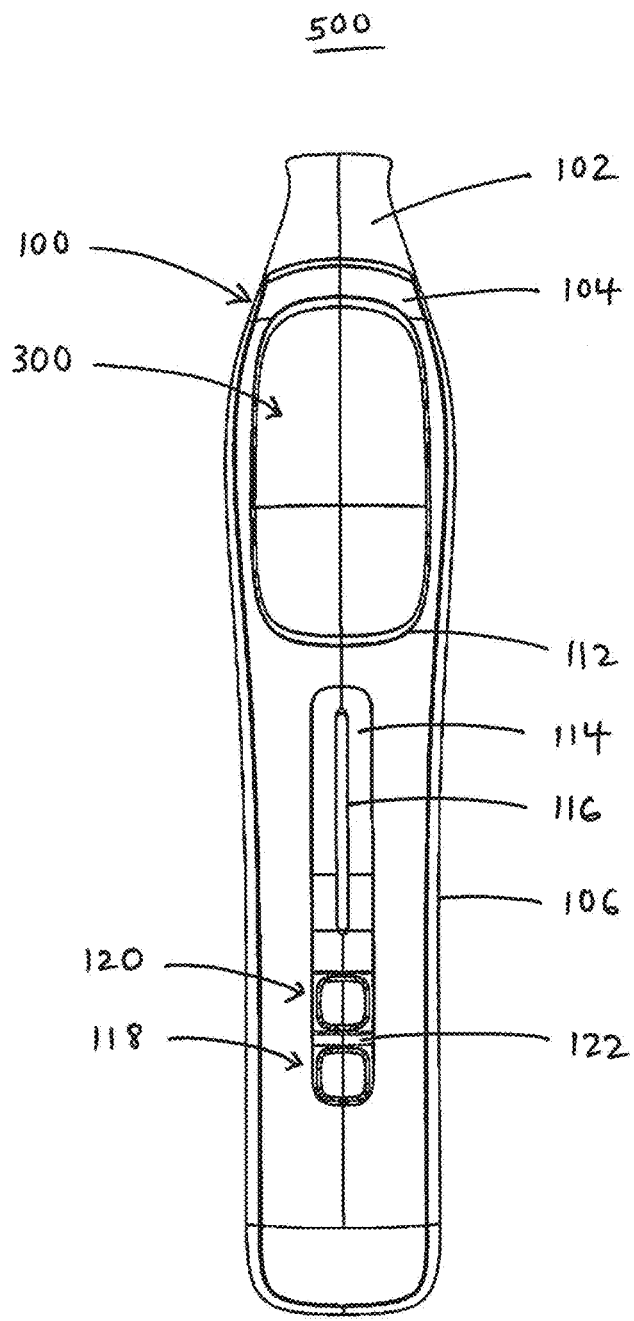
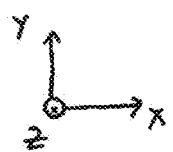

500

FIG. 19
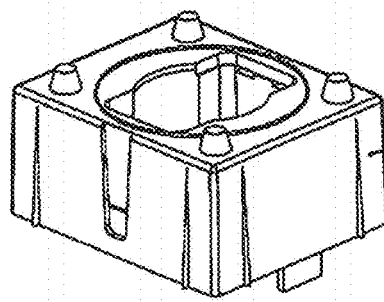
354
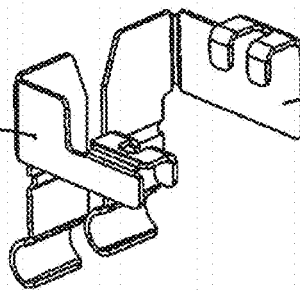
364
324a — 324b
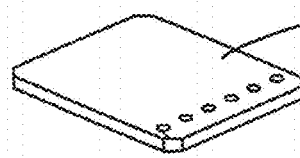
362
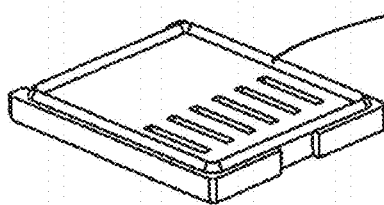
366
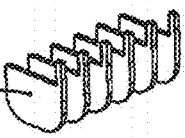
326

NON-NICOTINE POD ASSEMBLIES AND NON-NICOTINE E-VAPING DEVICES

BACKGROUND

Field

The present disclosure relates to non-nicotine electronic vaping (e-vaping) devices.

Description of Related Art

Some non-nicotine e-vaping devices include a first section coupled to a second section. The first section may include a wick and a heater. The wick is configured to move a non-nicotine pre-vapor formulation via capillary action and is positioned so as to extend into a reservoir and a vapor passage. The heater is in thermal contact with the wick and is configured to vaporize the non-nicotine pre-vapor formulation drawn via the wick into the vapor passage. The second section includes a power source configured to supply an electric current to the heater during vaping. The initiation of the operation of the non-nicotine e-vaping device may be achieved through manual- and/or puff-activation.

SUMMARY

At least one embodiment relates to a non-nicotine e-vaping device.

In an example embodiment, a non-nicotine e-vaping device may include a non-nicotine pod assembly and a device body configured to receive the non-nicotine pod assembly. The non-nicotine pod assembly is configured to hold a non-nicotine pre-vapor formulation. The non-nicotine pod assembly has an upstream end and a downstream end. The upstream end may define at least one upstream recess. The downstream end may define at least one downstream recess. The device body defines a through hole configured to receive the non-nicotine pod assembly. The through hole may include an upstream sidewall and a downstream sidewall. At least one of the upstream sidewall or the downstream sidewall may be configured to deflect during an insertion of the non-nicotine pod assembly. The upstream sidewall may include at least one upstream protrusion, and the downstream sidewall may include at least one downstream protrusion. The at least one upstream protrusion and the at least one downstream protrusion may be configured to engage with the at least one upstream recess and the at least one downstream recess, respectively, so as to retain the non-nicotine pod assembly within the through hole of the device body.

At least one embodiment relates to a device body for a non-nicotine e-vaping device.

In an example embodiment, a device body may include a device housing defining a through hole configured to receive a non-nicotine pod assembly. The through hole may include an upstream sidewall and a downstream sidewall. At least one of the upstream sidewall or the downstream sidewall is configured to deflect during an insertion of the non-nicotine pod assembly. The upstream sidewall includes at least one upstream protrusion, and the downstream sidewall includes at least one downstream protrusion. The at least one upstream protrusion and the at least one downstream protrusion are configured to engage with at least one upstream recess and at least one downstream recess, respectively, of the non-nicotine pod assembly so as to retain the non-nicotine pod assembly within the through hole.

At least one embodiment relates to a non-nicotine pod assembly for a non-nicotine e-vaping device.

In an example embodiment, a non-nicotine pod assembly may include a pod body configured to hold a non-nicotine pre-vapor formulation. The pod body may have a front face, a rear face, a first side face, a second side face, an upstream end, and a downstream end. The upstream end may include at least one electrical contact and may define at least one upstream recess. The downstream end may define a pod outlet and at least one downstream recess.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 1 is a front view of a non-nicotine e-vaping device according to an example embodiment.

FIG. 19 is an exploded view of the connector module of FIG. 17.

DETAILED DESCRIPTION

Figure 2:
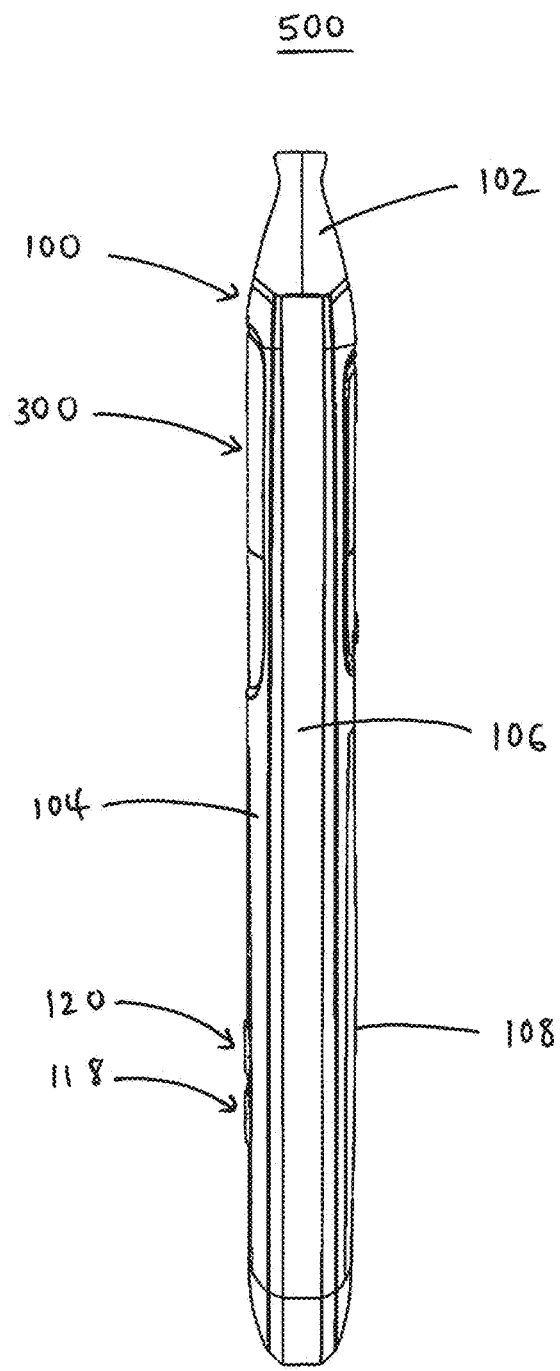
FIG. 2 is a side view of the non-nicotine e-vaping device of FIG. 1.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," "covering," etc. another element or layer, it may be directly on, connected to, coupled to, attached to, adjacent to, covering, etc. the other element or layer or intervening elements or layers may be present. In contrast, when an element is referred to as being "directly on," "directly connected to," "directly coupled to," etc. another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

When the term "same" or "identical" is used in the description of example embodiments, it should be understood that some imprecisions may exist. Thus, when one element or value is referred to as being the same as another element or value, it should be understood that the element or value is the same as the other element or value within a manufacturing or operational tolerance range (e.g., ±10%).

When the terms "about" or "substantially" are used in connection with a numerical value, it should be understood that the associated numerical value includes a manufacturing or operational tolerance (e.g., ±10%) around the stated numerical value. Moreover, when the words "generally" and "substantially" are used in connection with a geometric shape, it should be understood that the precision of the geometric shape is not required but that latitude for the shape is within the scope of the disclosure.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hardware may be implemented using processing or control circuitry such as, but not limited to, one or more processors, one or more Central Processing Units (CPUs), one or more microcontrollers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

Figure 3:
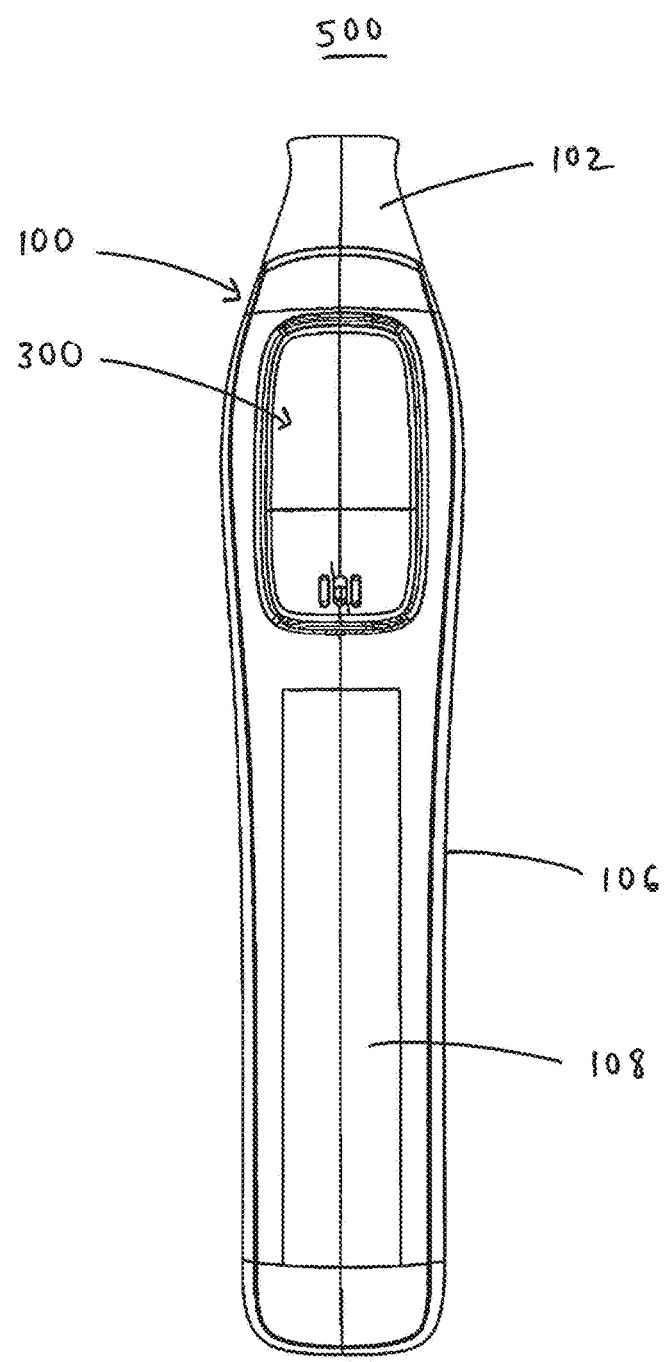
FIG. 3 is a rear view of the non-nicotine e-vaping device of FIG. 1.

FIG. 1 is a front view of a non-nicotine e-vaping device according to an example embodiment. FIG. 2 is a side view of the non-nicotine e-vaping device of FIG. 1. FIG. 3 is a rear view of the non-nicotine e-vaping device of FIG. 1. Referring to FIGS. 1-3, a non-nicotine e-vaping device 500 includes a device body 100 that is configured to receive a non-nicotine pod assembly 300. The non-nicotine pod assembly 300 is a modular article configured to hold a non-nicotine pre-vapor formulation. A non-nicotine pre-vapor formulation is a material or combination of materials that is devoid of nicotine and that may be transformed into a non-nicotine vapor. For example, the non-nicotine pre-vapor formulation may include a liquid, solid, and/or gel formulation. These may include, for example and without limitation, solutions and suspensions (e.g., emulsions) containing water, oil, beads, solvents, active ingredients, ethanol, plant extracts, non-nicotine compounds, natural or artificial flavors, vapor formers such as glycerin and propylene glycol, and/or any other ingredients that may be suitable for vaping. During vaping, the non-nicotine e-vaping device 500 is configured to heat the non-nicotine pre-vapor formulation to generate a non-nicotine vapor. Non-nicotine vapor, non-nicotine aerosol, and non-nicotine dispersion are used interchangeably and refer to the matter generated or outputted by the devices disclosed, claimed, and/or equivalents thereof, wherein such matter is devoid of nicotine.

As shown in FIGS. 1 and 3, the non-nicotine e-vaping device 500 extends in a longitudinal direction and has a length that is greater than its width. In addition, as shown in FIG. 2, the length of the non-nicotine e-vaping device 500 is also greater than its thickness. Furthermore, the width of the non-nicotine e-vaping device 500 may be greater than its thickness. Assuming an x-y-z Cartesian coordinate system, the length of the non-nicotine e-vaping device 500 may be measured in the y-direction, the width may be measured in the x-direction, and the thickness may be measured in the z-direction. The non-nicotine e-vaping device 500 may have a substantially linear form with tapered and/or rounded ends based on its front, side, and rear views, although example embodiments are not limited thereto.

The device body 100 includes a front cover 104, a frame 106, and a rear cover 108. The front cover 104, the frame 106, and the rear cover 108 form a device housing that encloses mechanical components, electronic components, and/or circuitry associated with the operation of the non-nicotine e-vaping device 500. For instance, the device housing of the device body 100 may enclose a power source configured to power the non-nicotine e-vaping device 500, which may include supplying an electric current to the non-nicotine pod assembly 300. In addition, when assembled, the front cover 104, the frame 106, and the rear cover 108 may constitute a majority of the visible portion of the device body 100. The device housing may be regarded as including all constituent parts of the device body 100 except for the mouthpiece 102. Stated differently, the mouthpiece 102 and the device housing may be regarded as forming the device body 100.

The front cover 104 (e.g., first cover) defines a primary opening configured to accommodate a bezel structure 112. The primary opening may have a rounded rectangular shape, although other shapes are possible depending on the shape of the bezel structure 112. The bezel structure 112 defines a through hole 150 configured to receive the non-nicotine pod assembly 300. The through hole 150 is discussed herein in more detail in connection with, for instance, FIG. 7.

The front cover 104 also defines a secondary opening configured to accommodate a light guide arrangement. The secondary opening may resemble a slot, although other shapes are possible depending on the shape of the light guide arrangement. In an example embodiment, the light guide arrangement includes a light guide housing 114 and a button housing 122. The light guide housing 114 is configured to expose a light guide lens 116. The button housing 122 may have an upstream portion structured as a first button 118 and a downstream portion structured as a second button 120. The button housing 122 may be in a form of a single structure or two separate structures. With the latter form, the first button 118 and the second button 120 can move with a more independent feel when pressed.

The operation of the non-nicotine e-vaping device 500 may be controlled by the first button 118 and the second button 120. For instance, the first button 118 may be a power button, and the second button 120 may be an intensity button. Although two buttons are shown in the drawings in connection with the light guide arrangement, it should be understood that more (or less) buttons may be provided depending on the available features and desired user interface.

The frame 106 (e.g., base frame) is the central support structure for the device body 100 (and the non-nicotine e-vaping device 500 as a whole). The frame 106 may be referred to as a chassis. The frame 106 includes a proximal end, a distal end, and a pair of side sections between the proximal end and the distal end. The proximal end and the distal end may also be referred to as the downstream end and the upstream end, respectively. As used herein, "proximal" (and, conversely, "distal") is in relation to an adult vaper during vaping, and "downstream" (and, conversely, "upstream") is in relation to a flow of the non-nicotine vapor. A bridging section may be provided between the opposing inner surfaces of the side sections (e.g., about midway along the length of the frame 106) for additional strength and stability. The frame 106 may be integrally formed so as to be a monolithic structure.

With regard to material of construction, the frame 106 may be formed of an alloy or a plastic. The alloy (e.g., die cast grade, machinable grade) may be an aluminum (Al) alloy or a zinc (Zn) alloy. The plastic may be a polycarbonate (PC), an acrylonitrile butadiene styrene (ABS), or a combination thereof (PC/ABS). For instance, the polycarbonate may be LUPOY SC1004A. Furthermore, the frame 106 may be provided with a surface finish for functional and/or aesthetic reasons (e.g., to provide a premium appearance). In an example embodiment, the frame 106 (e.g., when formed of an aluminum alloy) may be anodized. In another embodiment, the frame 106 (e.g., when formed of a zinc alloy) may be coated with a hard enamel or painted. In another embodiment, the frame 106 (e.g., when formed of a polycarbonate) may be metallized. In yet another embodiment, the frame 106 (e.g., when formed of an acrylonitrile butadiene styrene) may be electroplated. It should be understood that the materials of construction with regard to the frame 106 may also be applicable to the front cover 104, the rear cover 108, and/or other appropriate parts of the non-nicotine e-vaping device 500.

The rear cover 108 (e.g., second cover) also defines an opening configured to accommodate the bezel structure 112. The opening may have a rounded rectangular shape, although other shapes are possible depending on the shape of the bezel structure 112. In an example embodiment, the opening in the rear cover 108 is smaller than the primary opening in the front cover 104. In addition, although not shown, it should be understood that a light guide arrangement (e.g., including buttons) may be provided on the rear of the non-nicotine e-vaping device 500 in addition to (or in lieu of) the light guide arrangement on the front of the non-nicotine e-vaping device 500.

The front cover 104 and the rear cover 108 may be configured to engage with the frame 106 via a snap-fit arrangement. For instance, the front cover 104 and/or the rear cover 108 may include clips configured to interlock with corresponding mating members of the frame 106. In a non-limiting embodiment, the clips may be in a form of tabs with orifices configured to receive the corresponding mating members (e.g., protrusions with beveled edges) of the frame 106. Alternatively, the front cover 104 and/or the rear cover 108 may be configured to engage with the frame 106 via an interference fit (which may also be referred to as a press fit or friction fit). However, it should be understood that the front cover 104, the frame 106, and the rear cover 108 may be coupled via other suitable arrangements and techniques.

The device body 100 also includes a mouthpiece 102. The mouthpiece 102 may be secured to the proximal end of the frame 106. Additionally, as shown in FIG. 2, in an example embodiment where the frame 106 is sandwiched between the front cover 104 and the rear cover 108, the mouthpiece 102 may abut the front cover 104, the frame 106, and the rear cover 108. Furthermore, in a non-limiting embodiment, the mouthpiece 102 may be joined with the device housing via a bayonet connection.

Figure 4:
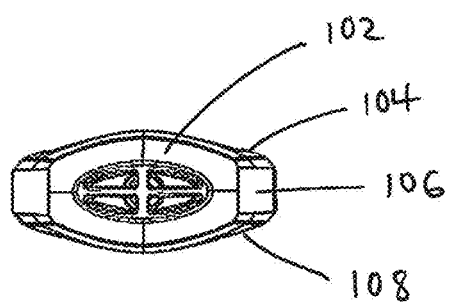
FIG. 4 is a proximal end view of the non-nicotine e-vaping device of FIG. 1.

FIG. 4 is a proximal end view of the non-nicotine e-vaping device of FIG. 1. Referring to FIG. 4, the outlet face of the mouthpiece 102 defines a plurality of vapor outlets. In a non-limiting embodiment, the outlet face of the mouthpiece 102 may be elliptically-shaped. In addition, the outlet face of the mouthpiece 102 may include a first crossbar corresponding to a major axis of the elliptically-shaped outlet face and a second crossbar corresponding to a minor axis of the elliptically-shaped outlet face. Furthermore, the first crossbar and the second crossbar may intersect perpendicularly and be integrally formed parts of the mouthpiece 102. Although the outlet face is shown as defining four vapor outlets, it should be understood that example embodiments are not limited thereto. For instance, the outlet face may define less than four (e.g., one, two) vapor outlets or more than four (e.g., six, eight) vapor outlets.

Figure 5:
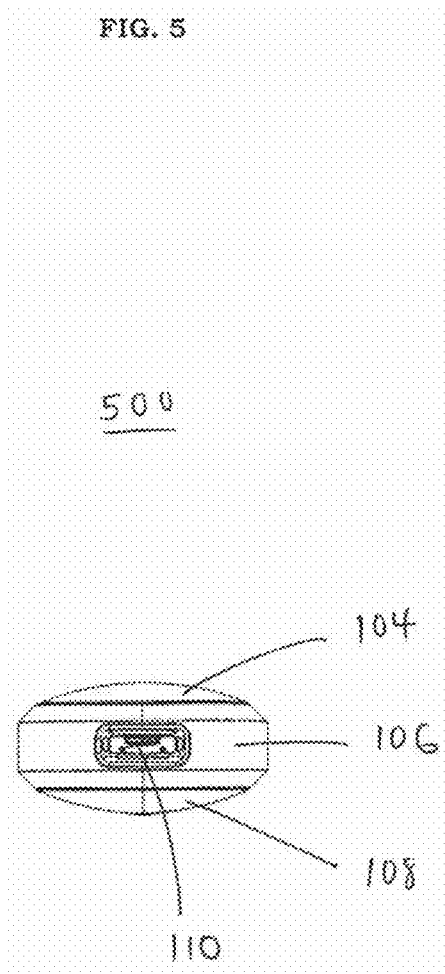
FIG. 5 is a distal end view of the non-nicotine e-vaping device of FIG. 1.

FIG. 5 is a distal end view of the non-nicotine e-vaping device of FIG. 1. Referring to FIG. 5, the distal end of the non-nicotine e-vaping device 500 includes a port 110. The port 110 is configured to receive an electric current (e.g., via a USB/mini-USB cable) from an external power source so as to charge an internal power source within the non-nicotine e-vaping device 500. In addition, the port 110 may also be configured to send data to and/or receive data (e.g., via a USB/mini-USB cable) from another non-nicotine e-vaping device or other electronic device (e.g., phone, tablet, computer). Furthermore, the non-nicotine e-vaping device 500 may be configured for wireless communication with another electronic device, such as a phone, via an application software (app) installed on that electronic device. In such an instance, an adult vaper may control or otherwise interface with the non-nicotine e-vaping device 500 (e.g., locate the non-nicotine e-vaping device, check usage information, change operating parameters) through the app.

Figure 6:
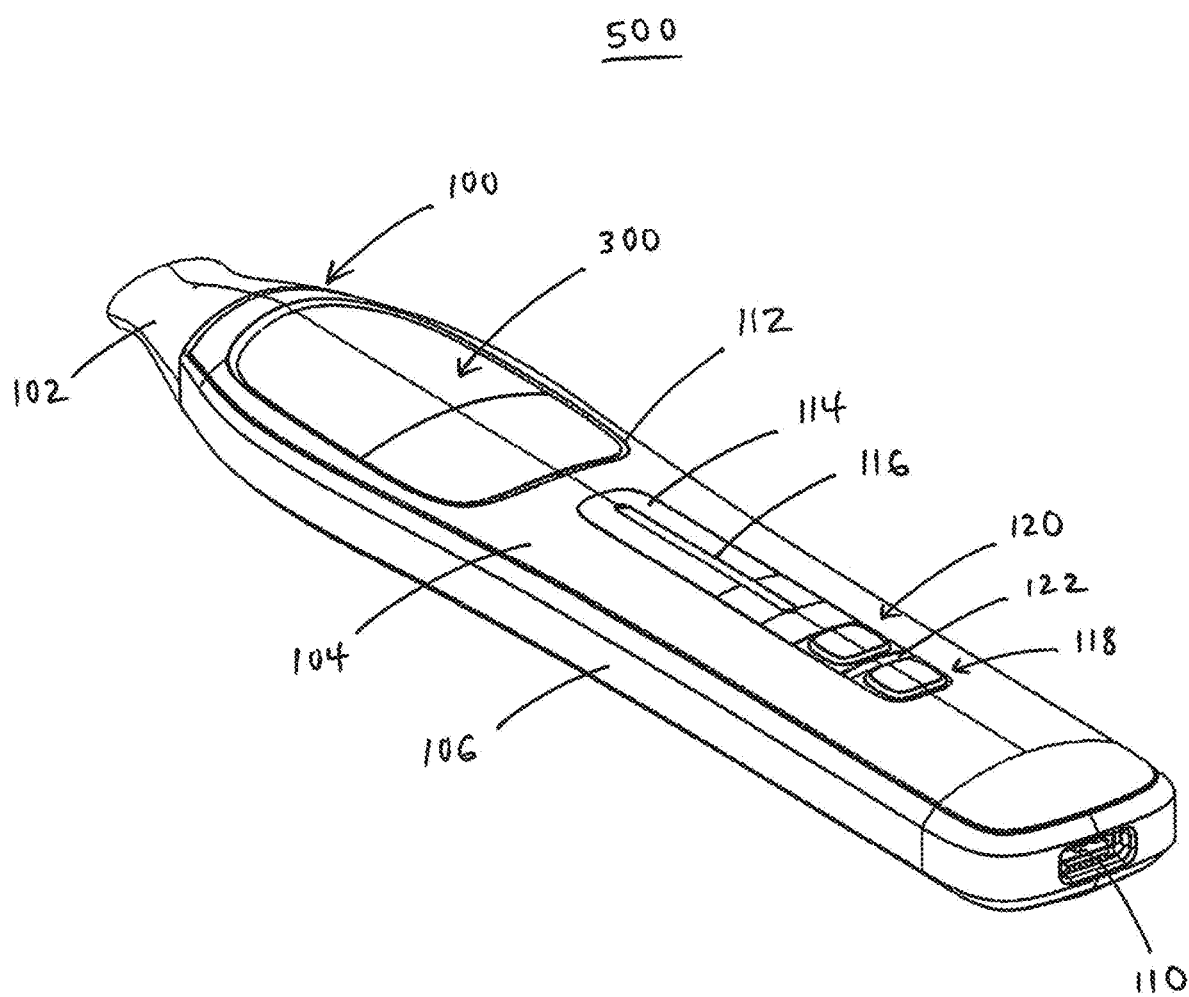
FIG. 6 is a perspective view of the non-nicotine e-vaping device of FIG. 1.

FIG. 6 is a perspective view of the non-nicotine e-vaping device of FIG. 1. Referring to FIG. 6, and as briefly noted above, the non-nicotine e-vaping device 500 includes a non-nicotine pod assembly 300 configured to hold a non-nicotine pre-vapor formulation. The non-nicotine pod assembly 300 has an upstream end (which faces the light guide arrangement) and a downstream end (which faces the mouthpiece 102). In a non-limiting embodiment, the upstream end is an opposing surface of the non-nicotine pod assembly 300 from the downstream end. The upstream end of the non-nicotine pod assembly 300 may define at least one upstream recess (e.g., first upstream recess 312a and/or second upstream recess 312b in FIG. 14), while the downstream end of the non-nicotine pod assembly 300 may define at least one downstream recess (e.g., first downstream recess 306a and/or second downstream recess 306b in FIG. 15). As will be discussed in more detail herein, the bezel structure 112 of the device body 100 may engage with the upstream end (e.g., via the at least one upstream recess) and the downstream end (e.g., via the at least one downstream recess) of the non-nicotine pod assembly 300 when the non-nicotine pod assembly 300 is seated within the device body 100.

The device body 100 and the non-nicotine pod assembly 300 include mechanical components, electronic components, and/or circuitry associated with the operation of the non-nicotine e-vaping device 500, which are discussed in more detail herein and/or are incorporated by reference herein. For instance, the non-nicotine pod assembly 300 may include mechanical components configured to actuate to release the non-nicotine pre-vapor formulation from a sealed reservoir within. The non-nicotine pod assembly 300 may also have mechanical aspects configured to engage with the device body 100 to facilitate the insertion and seating of the non-nicotine pod assembly 300.

Additionally, the non-nicotine pod assembly 300 may be a "smart pod" that includes electronic components and/or circuitry configured to store, receive, and/or transmit information to/from the device body 100. Such information may be used to authenticate the non-nicotine pod assembly 300 for use with the device body 100 (e.g., to prevent usage of an unapproved/counterfeit non-nicotine pod assembly). Furthermore, the information may be used to identify a type of the non-nicotine pod assembly 300 which is then correlated with a vaping profile based on the identified type. The vaping profile may be designed to set forth the general parameters for the heating of the non-nicotine pre-vapor formulation and may be subject to tuning, refining, or other adjustment by an adult vaper before and/or during vaping.

The non-nicotine pod assembly 300 may also communicate other information with the device body 100 that may be relevant to the operation of the non-nicotine e-vaping device 500. Examples of relevant information may include a level of the non-nicotine pre-vapor formulation within the non-nicotine pod assembly 300 and/or a length of time that has passed since the non-nicotine pod assembly 300 was inserted into the device body 100 and activated. For instance, if the non-nicotine pod assembly 300 was inserted into the device body 100 and activated more than a certain period of time prior (e.g., more than 6 months ago), the non-nicotine e-vaping device 500 may not permit vaping, and the adult vaper may be prompted to change to a new non-nicotine pod assembly even though the non-nicotine pod assembly 300 still contains adequate levels of non-nicotine pre-vapor formulation.

As noted supra and as will be discussed in more detail herein, the device body 100 may include mechanical components (e.g. complementary structures) configured to engage, hold, and/or activate the non-nicotine pod assembly 300. In addition, the device body 100 may include electronic components and/or circuitry configured to receive an electric current to charge an internal power source (e.g., battery) which, in turn, is configured to supply power to the non-nicotine pod assembly 300 during vaping. Furthermore, the device body 100 may include electronic components and/or circuitry configured to communicate with the non-nicotine pod assembly 300, a different non-nicotine e-vaping device, other electronic devices (e.g., phone, tablet, computer), and/or the adult vaper. The information being communicated may include pod-specific data, current vaping details, and/or past vaping patterns/history. The adult vaper may be notified of such communications with feedback that is haptic (e.g., vibrations), auditory (e.g., beeps), and/or visual (e.g., colored/blinking lights). The charging and/or communication of information may be performed with the port 110 (e.g., via a USB/mini-USB cable).

Figure 7:
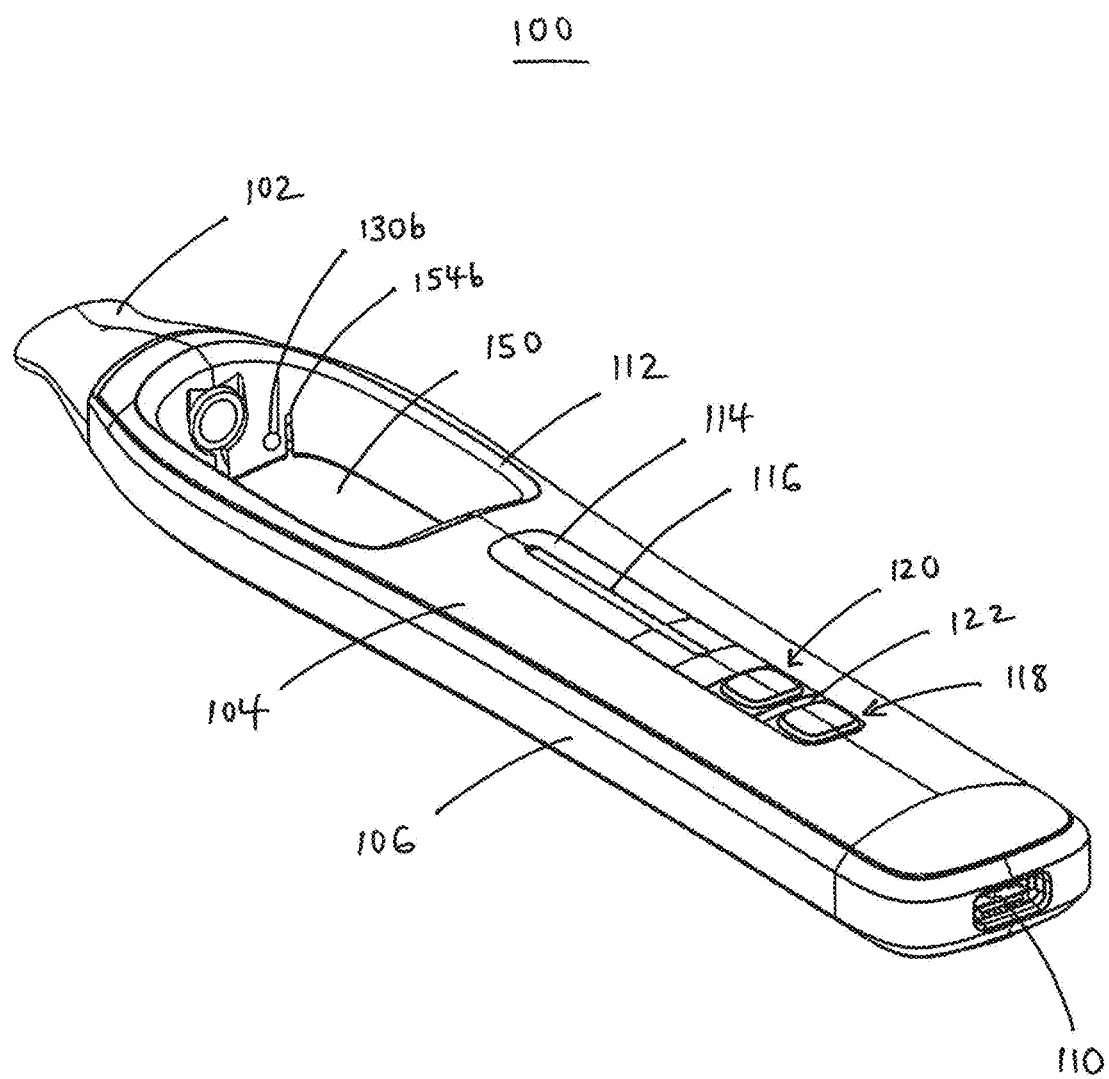
FIG. 7 is a perspective view of the device body of the non-nicotine e-vaping device of FIG. 6.
Figure 8:
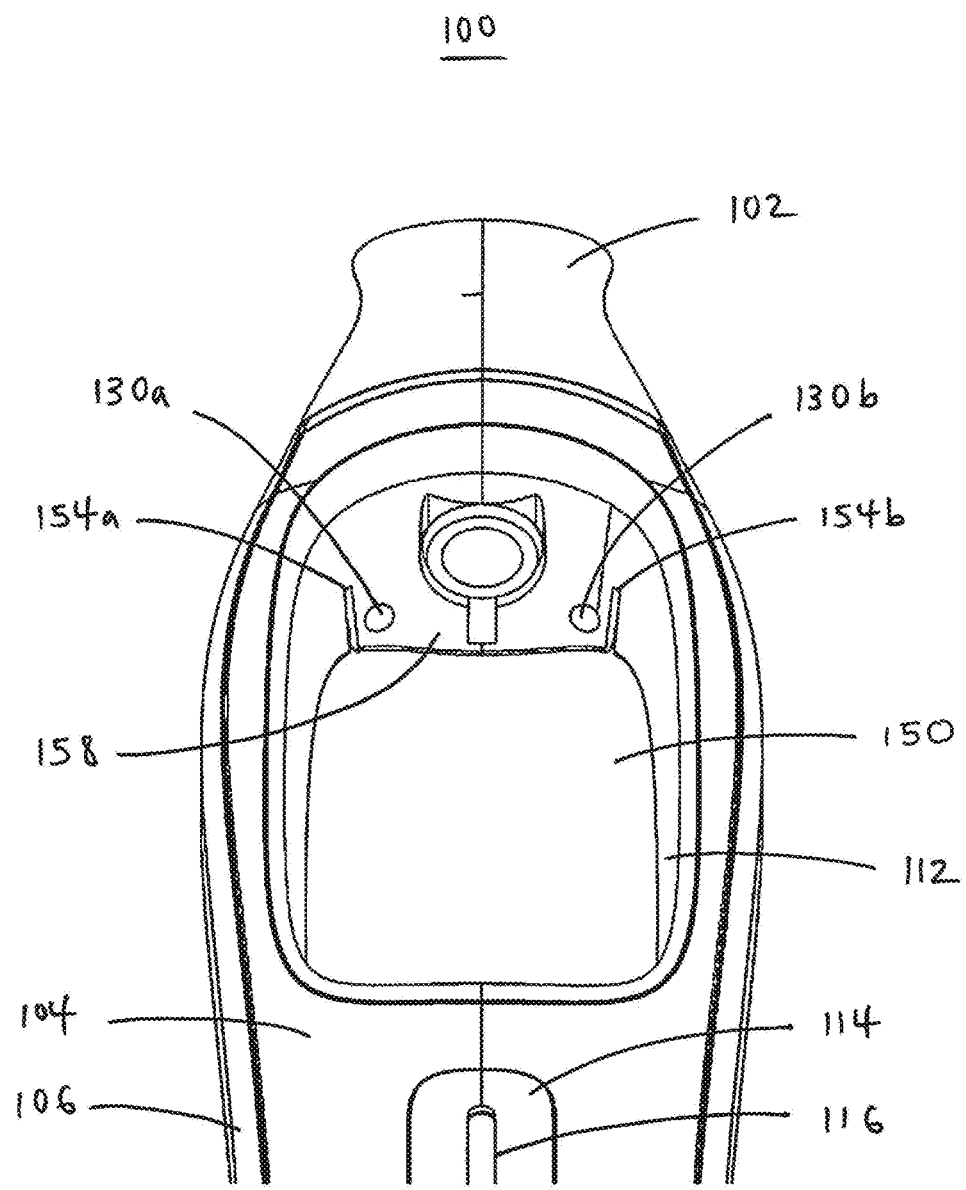
FIG. 8 is an enlarged view of the bezel structure in FIG. 7.
Figure 9:
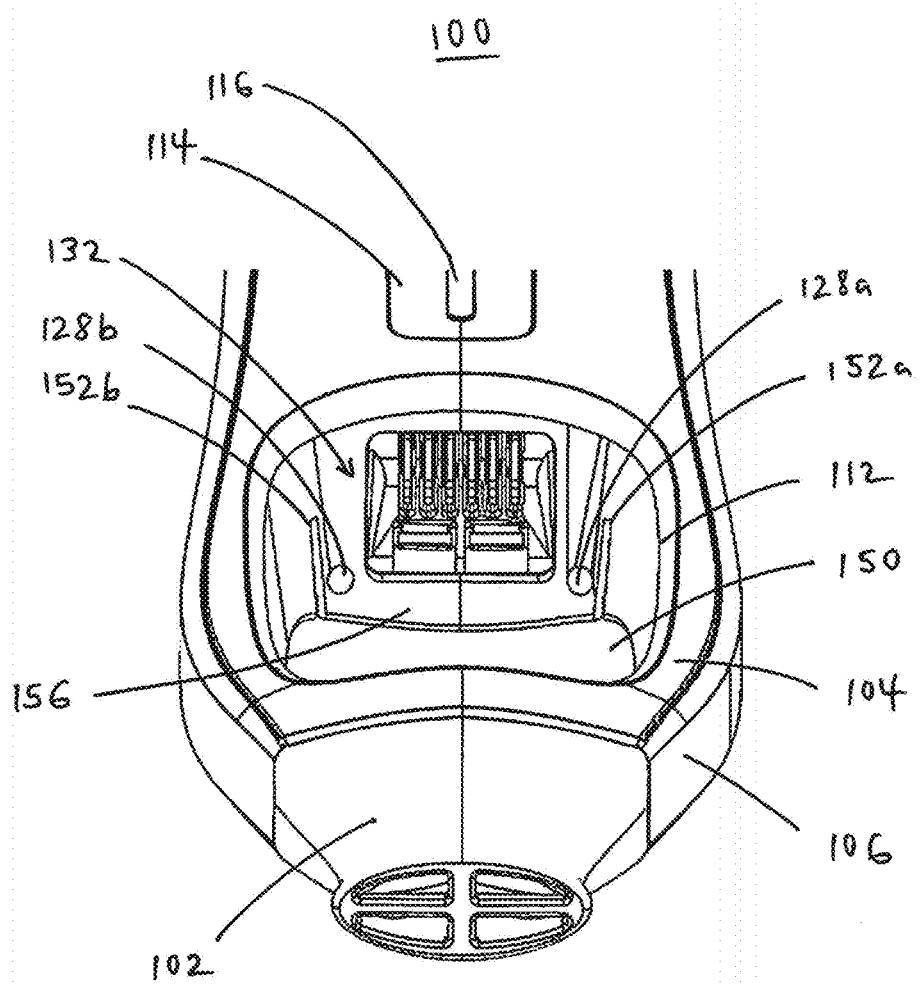
FIG. 9 is another enlarged view of the bezel structure in FIG. 7.

FIG. 7 is a perspective view of the device body of the non-nicotine e-vaping device of FIG. 6. FIG. 8 is an enlarged view of the bezel structure in FIG. 7. FIG. 9 is another enlarged view of the bezel structure in FIG. 7. Referring to FIGS. 7-9, the device body 100 defines a through hole 150 configured to receive the non-nicotine pod assembly 300. In an example embodiment, the bezel structure 112 of the device body 100 defines the through hole. The through hole 150 may have a rectangular shape with rounded corners, although other shapes are possible depending on the configuration of the non-nicotine pod assembly 300. The bezel structure 112 may be integrally formed so as to be a monolithic and resilient article with at least one flexible portion (e.g., upstream panel and/or downstream panel with protrusions) configured to engage with the non-nicotine pod assembly 300 when the non-nicotine pod assembly 300 is seated within the through hole 150. For instance, the bezel structure 112 may be formed of plastic. Accordingly, the non-nicotine pod assembly 300 may be positioned with relative ease and securely retained within the device body 100 in a cost-effective manner.

The bezel structure 112 has a length, a width, and a depth. The length of the bezel structure 112 may be in a longitudinal direction of the device body 100, while the width of the bezel structure 112 may be in a transverse direction across the through hole 150 and orthogonal to the longitudinal direction of the device body 100. The depth of the bezel structure 112 may be in a vertical direction through the through hole 150 and perpendicular to both the longitudinal direction of the device body 100 and the transverse direction across the through hole 150. For instance, assuming an x-y-z Cartesian coordinate system, the length of the bezel structure 112 may be measured in the y-direction, the width may be measured in the x-direction, and the depth may be measured in the z-direction. The length of the bezel structure 112 may be greater than the width, and the width of the bezel structure 112 may be greater than the depth.

As shown in FIG. 8, the bezel structure 112 may include a first downstream corner defining a first downstream slit 154a and a second downstream corner defining a second downstream slit 154b. Additionally, as shown in FIG. 9, the bezel structure 112 may include a first upstream corner defining a first upstream slit 152a and a second upstream corner defining a second upstream slit 152b. As a result, in an example embodiment where the bezel structure 112 has an upstream sidewall, an opposing downstream sidewall, and a pair of lateral sidewalls therebetween for defining the through hole 150, at least the upstream sidewall and/or the downstream sidewall may be configured to deflect (by virtue of the slits) during an insertion of the non-nicotine pod assembly 300. For instance, the upstream sidewall and the downstream sidewall of the bezel structure 112 may be configured to flex away from each other during the insertion of the non-nicotine pod assembly 300. Thus, the upstream sidewall and the downstream sidewall of the bezel structure 112 may be resilient sections configured to transition (e.g., reversibly) from an unloaded state to a loaded state when the non-nicotine pod assembly 300 is received by the device body 100.

In FIG. 8, the portion of the downstream sidewall between the first downstream slit 154a and the second downstream slit 154b may be a downstream engagement panel 158. Similarly, in FIG. 9, the portion of the upstream sidewall between the first upstream slit 152a and the second upstream slit 152b may be an upstream engagement panel 156. Each of the first upstream slit 152a, the second upstream slit 152b, the first downstream slit 154a, and the second downstream slit 154b may have a longest dimension (e.g., in the depth direction of the bezel structure 112) that is at least 30 percent (e.g., at least 40 percent) of the depth (e.g., average depth) of the bezel structure 112, although other dimensions are possible as long as the configuration permits a resilient lever-like action by the upstream engagement panel 156 and the downstream engagement panel 158.

The upstream sidewall and/or the downstream sidewall of the bezel structure 112 may include at least one protrusion (e.g., detent) configured to retain the non-nicotine pod assembly 300 within the through hole 150 of the device body 100 (e.g., via engagement with one or more recesses of the non-nicotine pod assembly 300). For instance, as illustrated in FIG. 8, the downstream engagement panel 158 of the downstream sidewall may include a first downstream protrusion 130a and a second downstream protrusion 130b. The first downstream protrusion 130a may be adjacent to the first downstream slit 154a and the rear side (e.g., rear cover 108) of the device body 100, while the second downstream protrusion 130b may be adjacent to the second downstream slit 154b and the rear side (e.g., rear cover 108) of the device body 100. Similarly, as illustrated in FIG. 9, the upstream engagement panel 156 of the upstream sidewall may include a first upstream protrusion 128a and a second upstream protrusion 128b. The first upstream protrusion 128a may be adjacent to the first upstream slit 152a and the rear side (e.g., rear cover 108) of the device body 100, while the second upstream protrusion 128b may be adjacent to the second upstream slit 152b and the rear side (e.g., rear cover 108) of the device body 100.

Although a pair of protrusions are illustrated in connection with each of the upstream sidewall and the downstream sidewall of the bezel structure 112, it should be understood that other quantities may also be suitable (e.g., one protrusion each, three protrusions each). Additionally, in an example embodiment, each of the protrusions may be in a form of a spherical cap (e.g., hemisphere). Alternatively, one or more of the protrusions may be in a form of an ellipsoidal cap (e.g., hemi-ellipsoid), a ridge (e.g., rounded, beveled), or other suitable mating structure for engaging with a corresponding recess of the non-nicotine pod assembly 300. Furthermore, the protrusion(s) may be an integral part of the bezel structure 112.

The first upstream protrusion 128a and the second upstream protrusion 128b are urged by the upstream engagement panel 156 of the upstream sidewall (e.g., from an unloaded state) to interlock with corresponding upstream recesses of the non-nicotine pod assembly 300 during the loaded state. Similarly, the first downstream protrusion 130a and the second downstream protrusion 130b are urged by the downstream engagement panel 158 of the downstream sidewall (e.g., from an unloaded state) to interlock with corresponding downstream recesses of the non-nicotine pod assembly 300 during the loaded state. Thus, in an example embodiment when the non-nicotine pod assembly 300 is seated within the through hole 150 of the device body 100, the non-nicotine pod assembly 300 is between and held (e.g., squeezed) by the upstream engagement panel 156 of the upstream sidewall and the downstream engagement panel 158 of the downstream sidewall.

When the non-nicotine pod assembly 300 is inserted into the through hole 150 of the device body 100, the upstream pair of protrusions (e.g., first upstream protrusion 128a and the second upstream protrusion 128b) of the bezel structure 112 may engage with the corresponding upstream pair of recesses of the non-nicotine pod assembly 300 before the downstream pair of protrusions (e.g., the first downstream protrusion 130a and the second downstream protrusion 130b) of the bezel structure 112 engages with the corresponding downstream pair of recesses of the non-nicotine pod assembly 300 (or vice versa). In another instance, the upstream and downstream pairs of protrusions of the bezel structure 112 may engage with the corresponding upstream and downstream pairs of recesses of the non-nicotine pod assembly 300 at substantially the same time when the non-nicotine pod assembly 300 is inserted into the through hole 150 of the device body 100. Furthermore, the engagement of the protrusions of the bezel structure 112 with the corresponding recesses of the non-nicotine pod assembly 300 may produce an auditory feedback (e.g., audible click) and/or a haptic feedback (e.g., vibration) to notify an adult vaper that the non-nicotine pod assembly 300 is properly seated in the through hole 150 of the device body 100.

Figure 11:
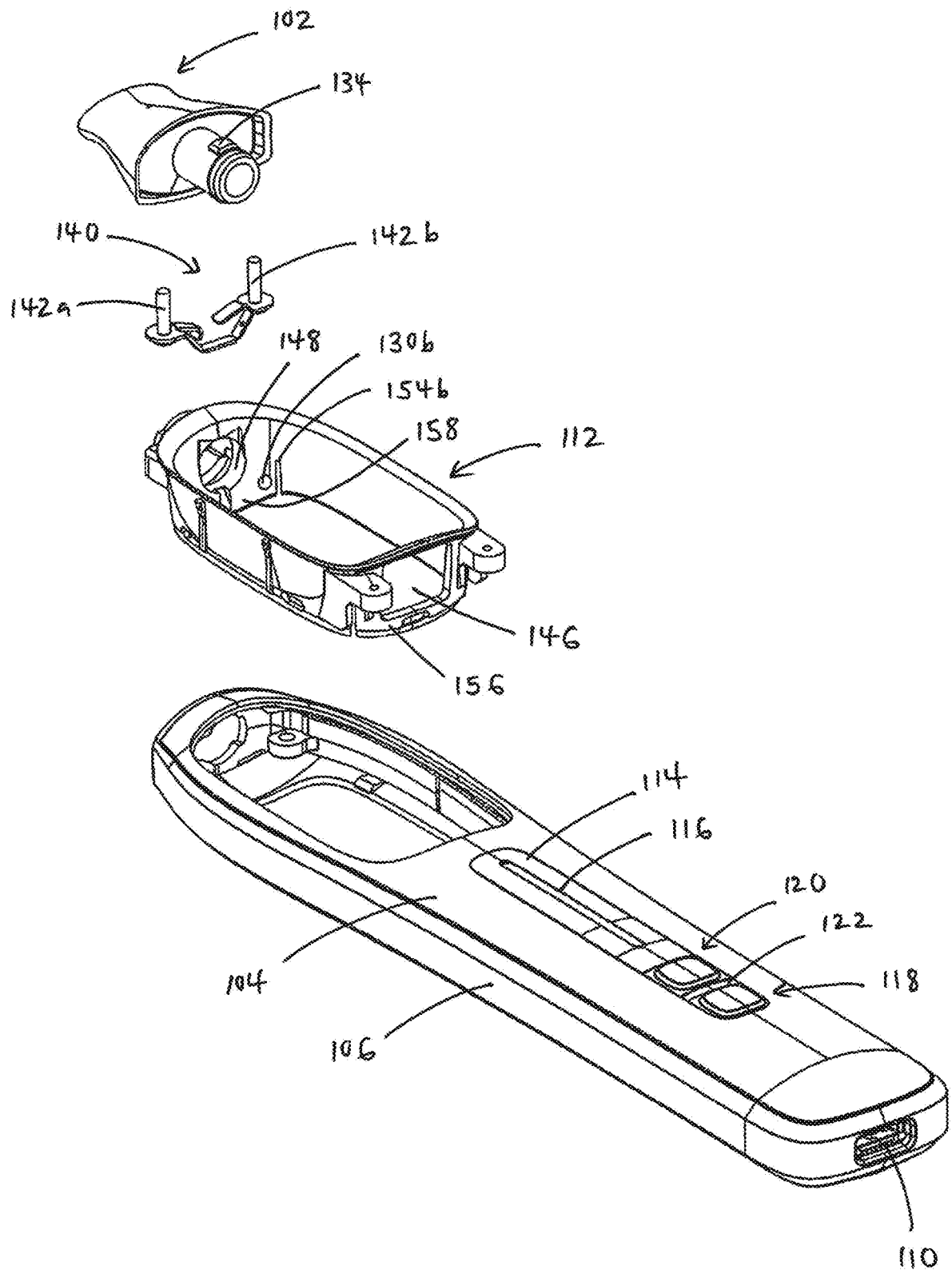
FIG. 11 is a partially exploded view involving the bezel structure in FIG. 9.

The downstream sidewall of the bezel structure 112 may define a downstream opening (e.g., downstream opening 148 in FIG. 11). As a result, in the example embodiment illustrated by FIGS. 7-8, a distal end of the mouthpiece 102 extends through the downstream opening of the bezel structure 112 and into the through hole 150 (e.g., so as to be between the first downstream slit 154a and the second downstream slit 154b). The distal end of the mouthpiece 102 may be in a form of an annular, elastic structure. Due to its elastic nature, the distal end of the mouthpiece 102 is able to temporarily deform so as to accommodate the insertion of the non-nicotine pod assembly 300 into the through hole 150 of the device body 100. In addition, the elasticity of the distal end of the mouthpiece 102 may help to establish a vapor-tight seal with the pod outlet of the non-nicotine pod assembly 300.

The device electrical contacts of the device body 100 are configured to engage with the pod electrical contacts of the non-nicotine pod assembly 300 when the non-nicotine pod assembly 300 is seated within the through hole 150 of the device body 100. The device electrical contacts of the device body 100 include a device electrical connector 132. Referring to FIG. 9, the device electrical connector 132 of the device body 100 is disposed at an upstream side of the through hole 150. The device electrical connector 132 of the device body 100 is configured to electrically engage with a non-nicotine pod assembly 300 that is seated within the through hole 150. As a result, power can be supplied from the device body 100 to the non-nicotine pod assembly 300 via the device electrical connector 132 during vaping. In addition, data can be sent to and/or received from the device body 100 and the non-nicotine pod assembly 300 via the device electrical connector 132.

The device electrical connector 132 includes power contacts and data contacts. The power contacts of the device electrical connector 132 are configured to supply power from the device body 100 to the non-nicotine pod assembly 300. As illustrated, the power contacts of the device electrical connector 132 include a first power contact and a second power contact, which may be positioned so as to be closer to the rear cover 108 than the front cover 104 (or vice versa). The first power contact may be adjacent to the first upstream protrusion 128a, while, the second power contact may be adjacent to the second upstream protrusion 128b. The first power contact and the second power contact of the device electrical connector 132 may be tractably-mounted and biased so as to protract into the through hole 150 as a default and to retract (e.g., independently) from the through hole 150 when subjected to a force that overcomes the bias.

The data contacts of the device electrical connector 132 are configured to transmit data between a non-nicotine pod assembly 300 and the device body 100. As illustrated, the data contacts of the device electrical connector 132 include a row of six projections, although example embodiments are not limited thereto. The data contacts of the device electrical connector 132 may be positioned so as to be closer to the front cover 104 than the rear cover 108 (or vice versa). The data contacts of the device electrical connector 132 may be distinct structures that, when assembled, extend into the through hole 150. The data contacts of the device electrical connector 132 may also be tractably-mounted and biased so as to protract into the through hole 150 as a default and to retract (e.g., independently) from the through hole 150 when subjected to a force that overcomes the bias.

For instance, when a non-nicotine pod assembly 300 is inserted into the through hole 150 of the device body 100, the pod electrical contacts of the non-nicotine pod assembly 300 will press against the corresponding device electrical contacts of the device body 100. As a result, the power contacts and the data contacts of the device electrical connector 132 will be retracted (e.g., at least partially retracted) into the device body 100 but will continue to push against the corresponding pod electrical contacts due to their resilient arrangement, thereby helping to ensure a proper electrical connection between the device body 100 and the non-nicotine pod assembly 300. Furthermore, such a connection may also be mechanically secure and have minimal contact resistance so as to allow power and/or signals between the device body 100 and the non-nicotine pod assembly 300 to be transferred and/or communicated reliably and accurately. While various aspects have been discussed in connection with the device electrical contacts of the device body 100, it should be understood that example embodiments are not limited thereto and that other configurations may be utilized.

Figure 10:
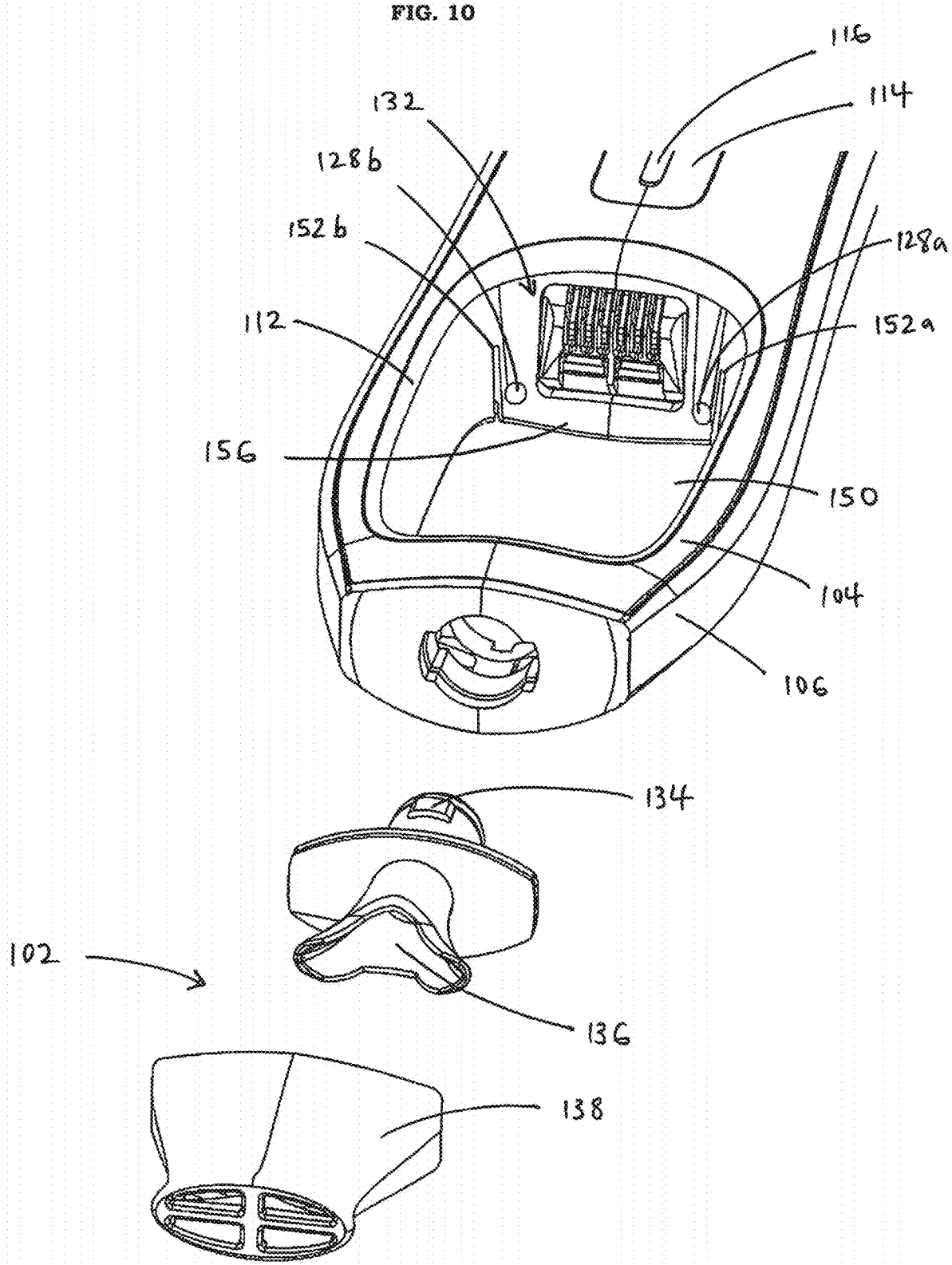
FIG. 10 is a partially exploded view involving the mouthpiece in FIG. 9.

FIG. 10 is a partially exploded view involving the mouthpiece in FIG. 9. Referring to FIG. 10, the mouthpiece 102 is configured to extend through the frame 106 of the device housing and engage with the bezel structure 112. As will be discussed in more detail herein, the mouthpiece 102 may be an assembly of several distinct parts. Alternatively, the mouthpiece 102 may be a single, integrally-formed structure. In an example embodiment, the proximal ends of the frame 106 and the bezel structure 112 are configured to receive a distal end of the mouthpiece 102. As illustrated, each of the proximal ends of the frame 106 and the bezel structure 112 may be a female end, while the distal end of the mouthpiece may be a male end.

For instance, the mouthpiece 102 may be secured, mated, or coupled (e.g., reversibly coupled) to the bezel structure 112 with a bayonet connection. In such an instance, the female end of the bezel structure 112 may define a pair of opposing L-shaped slots, while the male end of the mouthpiece 102 may have opposing radial members 134 (e.g., radial pins) configured to engage with the L-shaped slots of the bezel structure 112. Each of the L-shaped slots of the bezel structure 112 may have a longitudinal portion and a circumferential portion. Optionally, the terminus of the circumferential portion may have a serif portion to help reduce or prevent the likelihood that that a radial member 134 of the mouthpiece 102 will inadvertently become disengaged.

In a non-limiting embodiment, the longitudinal portions of the L-shaped slots extend in parallel and along a longitudinal axis of the device body 100, while the circumferential portions of the L-shaped slots extend around the longitudinal axis (e.g., central axis) of the device body 100. As a result, to couple the mouthpiece 102 to the device housing, the mouthpiece 102 is initially rotated 90 degrees to align the radial members 134 with the downstream opening in the proximal end of the frame 106 and the entrances to the longitudinal portions of the L-shaped slots of the bezel structure 112 (e.g., based on the view in FIG. 10). The mouthpiece 102 is then inserted through the frame 106 and into the bezel structure 112 such that the radial members 134 slide along the longitudinal portions of the L-shaped slots until the junction with each of the circumferential portions is reached. At this point, the mouthpiece 102 is then rotated such that the radial members 134 travel across the circumferential portions until the terminus of each is reached. Where a serif portion is present at each terminus, a haptic and/or auditory feedback (e.g., audible click) may be produced to notify an adult vaper that the mouthpiece 102 has been properly coupled to the device housing. Although a pair of radial members 134 and a corresponding pair of L-shaped slots are discussed herein, it should be understood that, in some instances, one radial member 134 and one corresponding L-shaped slot is adequate.

The mouthpiece 102 defines a vapor passage 136 through which non-nicotine vapor flows during vaping. The vapor passage 136 is in fluidic communication with the through hole 150 (which is where the non-nicotine pod assembly 300 is seated within the device body 100). The proximal end of the vapor passage 136 may include a flared portion. In addition, the mouthpiece 102 may include an end cover 138. The end cover 138 may taper from its distal end to its proximal end. The outlet face of the end cover 138 defines a plurality of vapor outlets. Although four vapor outlets are shown in the end cover 138, it should be understood that example embodiments are not limited thereto.

Figure 12:
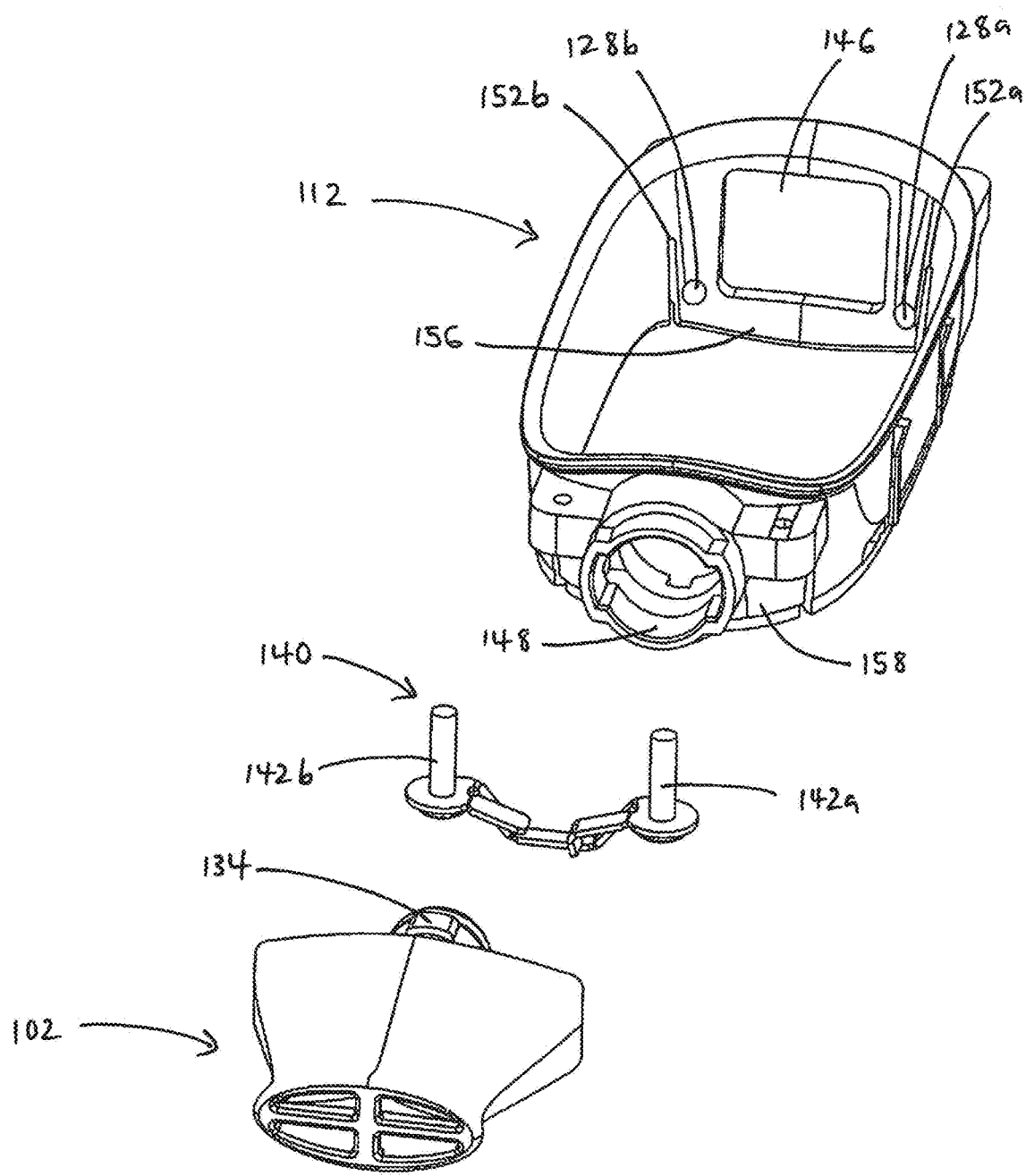
FIG. 12 is an enlarged perspective view of the mouthpiece, retention structure, and bezel structure in FIG. 11.

FIG. 11 is a partially exploded view involving the bezel structure in FIG. 9. FIG. 12 is an enlarged perspective view of the mouthpiece, retention structure, and bezel structure in FIG. 11. Referring to FIGS. 11-12, the bezel structure 112 includes an upstream sidewall and a downstream sidewall. The upstream sidewall of the bezel structure 112 defines a connector opening 146. The connector opening 146 is configured to expose or receive the device electrical connector 132 of the device body 100. The downstream sidewall of the bezel structure 112 defines a downstream opening 148. The downstream opening 148 of the bezel structure 112 is configured to receive the distal end of the mouthpiece 102.

To facilitate an attachment to the device housing, the bezel structure 112 has an upstream pair of tabs and a downstream pair of tabs (e.g., external tabs). The upstream pair of tabs may be adjacent to the connector opening 146 (e.g., one tab on each side of the connector opening 146), while the downstream pair of tabs may be adjacent to the downstream opening 148 (e.g., one tab on each side of the downstream opening 148). Similarly, the frame 106 of the device housing has an upstream pair of tabs and a downstream pair of tabs (e.g., internal tabs) which correspond to the upstream pair of tabs and the downstream pair of tabs, respectively, of the bezel structure 112. The bezel structure 112 may be secured to the frame 106 of the device housing via the above tabs with at least a retention structure 140.

The retention structure 140 may include a first fastener 142a, a second fastener 142b, and a catch mechanism (e.g., as an intermediate, linking member). In an example embodiment, the first fastener 142a and the second fastener 142b may be separate parts (e.g., screws) that extend through apertures in the opposite ends of the catch mechanism. The downstream pair of tabs of the bezel structure 112 may be secured to the corresponding downstream pair of tabs of the frame 106 with the first fastener 142a and the second fastener 142b of the retention structure 140. Likewise, although not specifically exploded for viewing in FIG. 11, the upstream pair of tabs of the bezel structure 112 may be secured to the corresponding upstream pair of tabs of the frame 106 with upstream fasteners similar or identical to the first fastener 142a and the second fastener 142b.

As shown in FIG. 12, the proximal, female end of the bezel structure 112 may be a cylindrical section that defines the downstream opening 148 as well as the pair of opposing L-shaped slots for establishing a bayonet connection with the opposing radial members 134 of the mouthpiece 102. In an example embodiment, one of the circumferential portions of the L-shaped slots may be an open portion of the cylindrical section (e.g., open portion in the underside of the cylindrical section based on the view in FIG. 12). In such an instance, when the downstream pair of tabs of the bezel structure 112 are secured to the corresponding downstream pair of tabs of the frame 106 by the retention structure 140, the catch mechanism (which links the first fastener 142a and the second fastener 142b) will align with the open portion of the cylindrical section so as to define at least a part of the circumferential portion of one of the L-shaped slots. The catch mechanism of the retention structure 140 includes two angled fingers separated by a gap that corresponds to approximately a width of one of the radial members 134 of the mouthpiece 102. The two angled fingers of the catch mechanism are resilient and configured to flex when the mouthpiece 102 is rotated (e.g., during assembly) in order to accommodate the circumferential motion of a corresponding one of the radial members 134. When the corresponding radial member 134 reaches the gap between the two angled fingers of the catch mechanism (of the retention structure 140), the angled finger that was flexed will rebound or spring back to its unloaded state so as to seat (e.g., catch) the radial member 134 within the gap. In the seated position, the two angled fingers of the catch mechanism may abut or be adjacent to the sides of the corresponding radial member 134 so as to resist a further rotation of the mouthpiece 102. As a result, the bayonet connection between the mouthpiece 102 and the bezel structure 112 may be maintained in a relatively secure manner by the retention structure 140.

During assembly, the bezel structure 112 may be secured to the frame 106 (along with other mechanical components, electronic components, and/or circuitry) before the front cover 104 and the rear cover 108 are attached to the frame 106. For instance, the bezel structure 112 may be initially positioned relative to the frame 106 such that the downstream tabs and the upstream tabs of the bezel structure 112 are aligned with the downstream tabs and the upstream tabs, respectively, of the frame 106. In an example embodiment where each of the tabs has an orifice (e.g., preformed orifice) extending therethrough, the orifices in the downstream tabs and the orifices in the upstream tabs may be placed in alignment as a result. Once the proper alignment is achieved, the first fastener 142a and the second fastener 142b may be introduced through the downstream tabs of the frame 106 and then through the downstream tabs of the bezel structure 112 (e.g., via the underside of the tabs based on the view in FIG. 11). Similarly, upstream fasteners may be introduced through the upstream tabs of the frame 106 and then through the upstream tabs of the bezel structure 112 in a like manner. Although FIG. 11 shows the device housing as already being assembled before the attachment of the bezel structure 112, it should be understood that this partially exploded view is merely intended to show certain parts (e.g., bezel structure 112) separately from the other parts of the device body 100 and, thus, is not necessarily representative of the order of assembling the device body 100.

Figure 13:
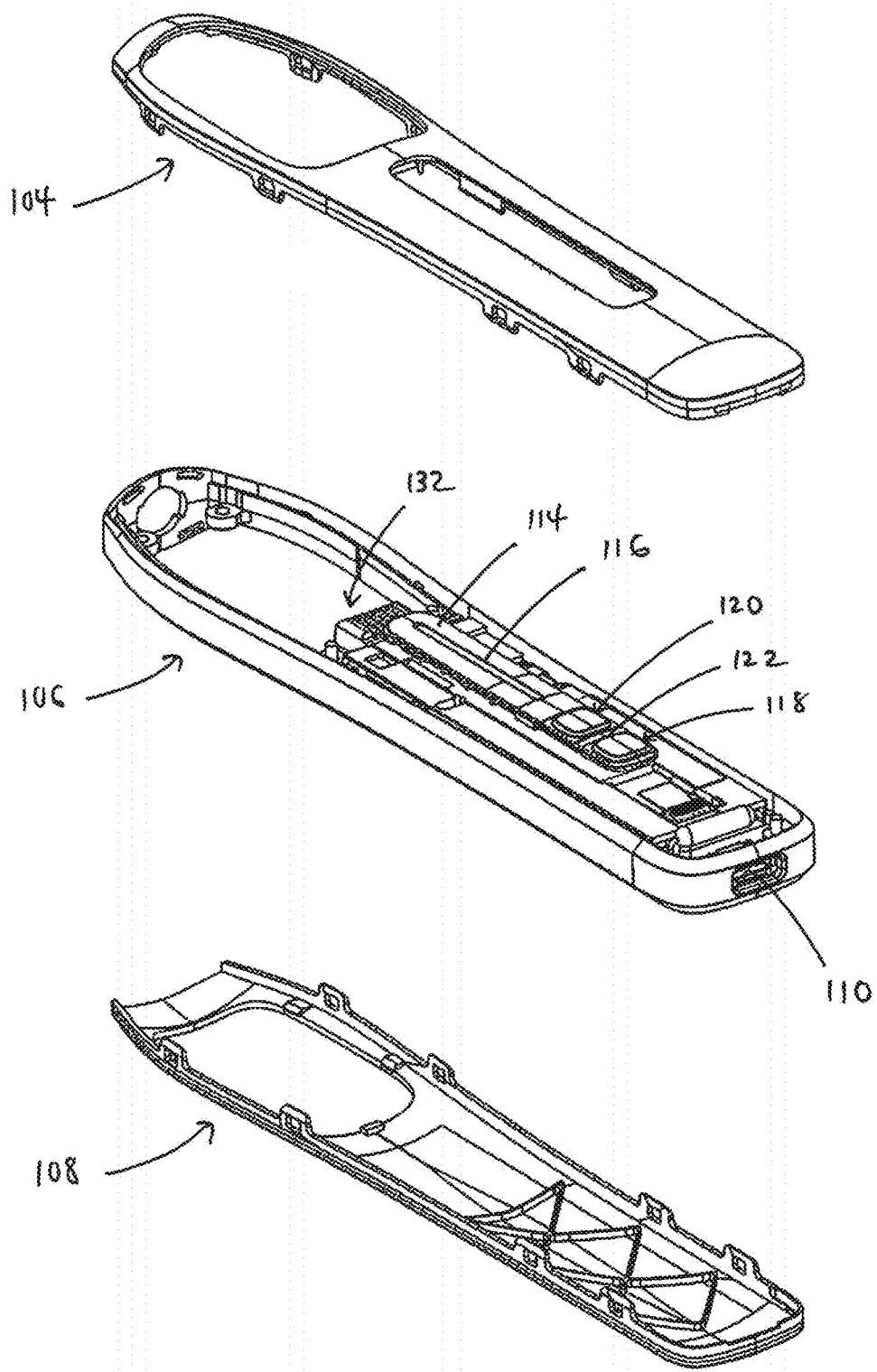
FIG. 13 is a partially exploded view involving the front cover, the frame, and the rear cover in FIG. 11.

FIG. 13 is a partially exploded view involving the front cover, the frame, and the rear cover in FIG. 11. Referring to FIG. 13, various mechanical components, electronic components, and/or circuitry associated with the operation of the non-nicotine e-vaping device 500 may be secured to the frame 106. The front cover 104 and the rear cover 108 may be configured to engage with the frame 106 via a snap-fit arrangement. In an example embodiment, the front cover 104 and the rear cover 108 include clips configured to interlock with corresponding mating members of the frame 106. The clips may be in a form of tabs with orifices configured to receive the corresponding mating members (e.g., protrusions with beveled edges) of the frame 106. The front cover 104 has two rows with four clips each (for a total of eight clips for the front cover 104). Similarly, the rear cover 108 has two rows with four clips each (for a total of eight clips for the rear cover 108). The corresponding mating members of the frame 106 may be on the inner sidewalls of the frame 106. As a result, the engaged clips and mating members may be hidden from view when the front cover 104 and the rear cover 108 are snapped together. Alternatively, the front cover 104 and/or the rear cover 108 may be configured to engage with the frame 106 via an interference fit. However, it should be understood that the front cover 104, the frame 106, and the rear cover 108 may be coupled via other suitable arrangements and techniques.

Figure 14:
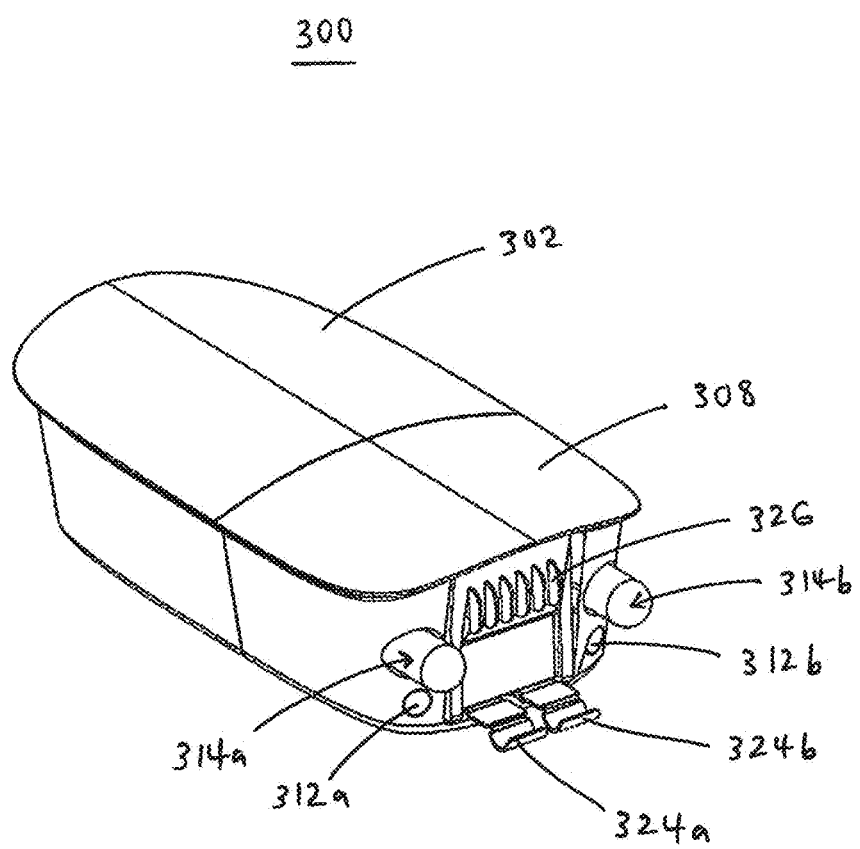
FIG. 14 is a perspective view of the non-nicotine pod assembly of the non-nicotine e-vaping device in FIG. 6.
Figure 15:
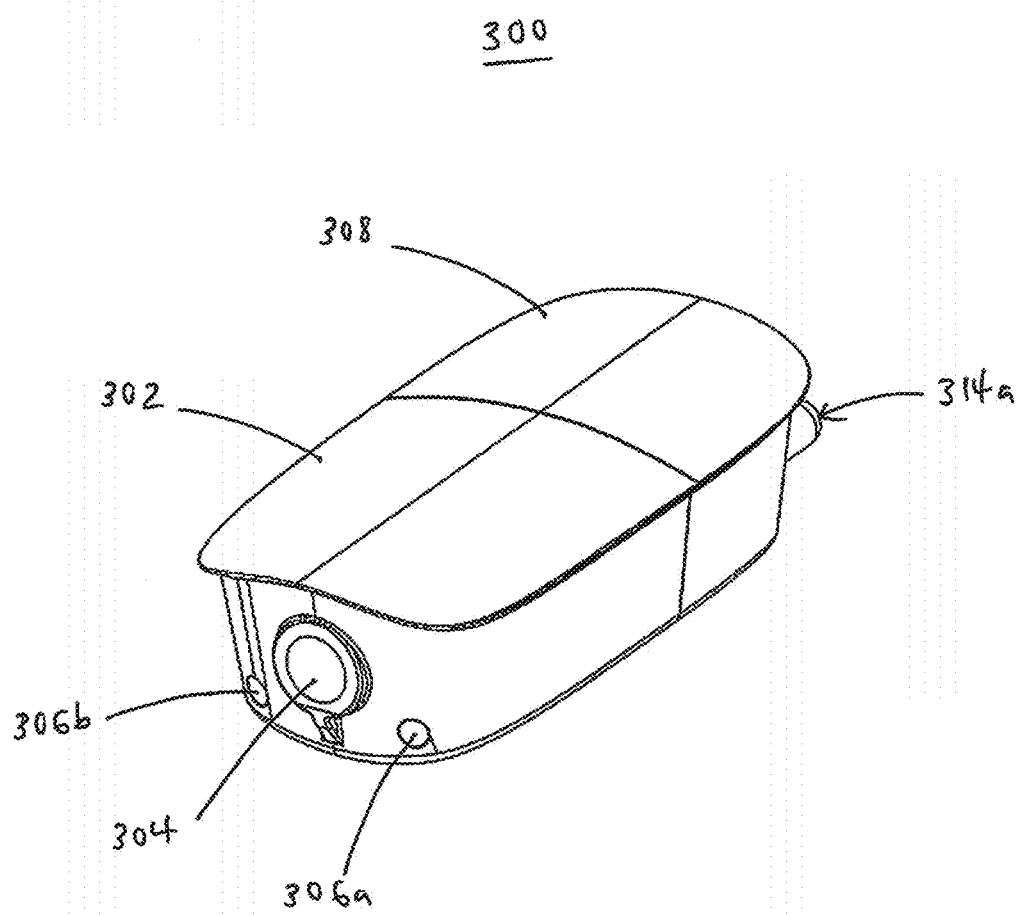
FIG. 15 is another perspective view of the non-nicotine pod assembly of FIG. 14.

FIG. 14 is a perspective view of the non-nicotine pod assembly of the non-nicotine e-vaping device in FIG. 6. FIG. 15 is another perspective view of the non-nicotine pod assembly of FIG. 14. Referring to FIGS. 14-15, the non-nicotine pod assembly 300 has a pod body including a front face, a rear face opposite the front face, a first side face between the front face and the rear face, a second side face opposite the first side face, an upstream end face, and a downstream end face opposite the upstream end face. The corners of the side and end faces (e.g., corner of the first side face and the upstream end face, corner of upstream end face and the second side face, corner of the second side face and the downstream end face, corner of the downstream end face and the first side face) may be rounded. However, in some instances, the corners may be angular. In addition, the peripheral edge of the front face may be in a form of a ledge. The front face of the non-nicotine pod assembly 300 may be wider and longer than the rear face. In such an instance, the first side face and the second side face may be angled inwards towards each other. The upstream end face and the downstream end face may also be angled inwards towards each other. Because of the angled faces, the insertion of the non-nicotine pod assembly 300 will be unidirectional (e.g., from the front side (side associated with the front cover 104) of the device body 100). As a result, the possibility that the non-nicotine pod assembly 300 will be improperly inserted into the device body 100 can be reduced or prevented.

The upstream end of the non-nicotine pod assembly 300, as illustrated by FIG. 14, may include at least one electrical contact and may define at least one upstream recess (e.g., first upstream recess 312*a* and/or second upstream recess 312*b*), while the downstream end of the non-nicotine pod assembly 300, as illustrated by FIG. 15, may define a pod outlet 304 and at least one downstream recess (e.g., first downstream recess 306*a* and/or second downstream recess 306*b*). The pod body of the non-nicotine pod assembly 300 may include a first housing section 302 and a second housing section 308. The first housing section 302 of the pod body may be configured to hold a non-nicotine pre-vapor formulation, while the second housing section 308 may be configured to receive a connector module 320 (e.g., FIG. 17).

In an example embodiment, the upstream end of the second housing section 308 of the pod body defines a cavity, while the downstream end of the first housing section 302 of the pod body defines a pod outlet 304 that is in fluidic communication with the cavity in the second housing section 308. As will be described in more detail herein, a connector module 320 (e.g., FIG. 17) is configured to be seated within the cavity of the second housing section 308 of the pod body. The connector module 320 includes an external face (e.g., with electrical contacts) and adjacent side faces. When the non-nicotine pod assembly 300 is assembled, the external face of the connector module 320 forms an exterior of the non-nicotine pod assembly 300, while the adjacent side faces are hidden from view within the cavity of the second housing section 308. Thus, the external face of the connector module 320 may be part of the upstream end face of the non-nicotine pod assembly 300.

The external face of the connector module 320 may include at least one electrical contact. The at least one electrical contact may include a plurality of power contacts. For instance, the plurality of power contacts may include a first power contact 324*a* and a second power contact 324*b*. Although the first power contact 324*a* and the second power contact 324*b* are illustrated in FIG. 14 as extending outward in a horizontal manner, it should be understood that, in a further form of the non-nicotine pod assembly 300, the first power contact 324*a* and the second power contact 324*b* may be folded upwards so as to be against the external face and adjacent to the data contacts 326 of the connector module 320. The first power contact 324*a* of the non-nicotine pod assembly 300 is configured to electrically connect with the first power contact of the device electrical connector 132 of the device body 100 (e.g., power contact adjacent to the first upstream protrusion 128*a* in FIG. 9). Similarly, the second power contact 324*b* of the non-nicotine pod assembly 300 is configured to electrically connect with the second power contact of the device electrical connector 132 of the device body 100 (e.g., power contact adjacent to the second upstream protrusion 128*b* in FIG. 9). In addition, the at least one electrical contact of the non-nicotine pod assembly 300 includes a plurality of data contacts 326. The plurality of data contacts 326 of the non-nicotine pod assembly 300 are configured to electrically connect with the data contacts of the device electrical connector 132 (e.g., row of six contacts in FIG. 9). While two power contacts and six data contacts are shown in connection with the non-nicotine pod assembly 300, it should be understood that other variations are possible depending on the design of the device body 100.

As noted supra, the pod body of the non-nicotine pod assembly 300 may include a first housing section 302 and a second housing section 308. The first housing section 302 has a downstream end defining the pod outlet 304. The rim of the pod outlet 304 may optionally be a raised region. In such an instance, if the downstream end face of the first housing section 302 is angled inwards, then the degree of protrusion of the rim of the pod outlet 304 may be greater towards the rear face and less towards the front face. In addition, the rear-facing side of the pod outlet 304 may have a ramp that leads upward from the downstream end face to the rim. As a result, when the non-nicotine pod assembly 300 is being inserted into the through hole 150 of the device body 100, the advancement of the pod outlet 304 into alignment with the distal end of the mouthpiece 102 may be facilitated by the ramp. In a non-limiting embodiment, the distal end of the mouthpiece 102 may include (or be formed of) a resilient material to help accommodate the advancement of the non-nicotine pod assembly 300 into the through hole 150 of the device body 100 and to create a seal around the pod outlet 304.

The downstream end of the first housing section 302 additionally defines at least one downstream recess. In an example embodiment, the at least one downstream recess is in a form of a first downstream recess 306*a* and a second downstream recess 306*b*. The pod outlet 304 may be between the first downstream recess 306*a* and the second downstream recess 306*b*. The first downstream recess 306*a* and the second downstream recess 306*b* are configured to engage with the first downstream protrusion 130*a* and the second downstream protrusion 130*b*, respectively, of the device body 100. The first downstream recess 306*a* and the second downstream recess 306*b* may each be in a form of a dimple. In such an instance, each of the first downstream protrusion 130*a* and the second downstream protrusion 130*b* of the device body 100 may be in a form of a rounded structure (e.g., spherical cap) configured to engage with a corresponding one of the first downstream recess 306a and the second downstream recess 306b.

Similarly, the upstream end of the second housing section 308 defines at least one upstream recess. In an example embodiment, the at least one upstream recess is in a form of a first upstream recess 312a and a second upstream recess 312b. The first power contact 324a and the second power contact 324b of the connector module 320 may be between the first upstream recess 312a and the second upstream recess 312b. The first upstream recess 312a and the second upstream recess 312b are configured to engage with the first upstream protrusion 128a and the second upstream protrusion 128b, respectively, of the device body 100. The first upstream recess 312a and the second upstream recess 312b may each also be in a form of a dimple. In such an instance, each of the first upstream protrusion 128a and the second upstream protrusion 128b of the device body 100 may be in a form of a rounded structure (e.g., spherical cap) configured to engage with a corresponding one of the first upstream recess 312a and the second upstream recess 312b.

The first housing section 302 may define a reservoir within configured to hold the non-nicotine pre-vapor formulation. The reservoir may be configured to hermetically seal the non-nicotine pre-vapor formulation until an activation of the non-nicotine pod assembly 300 to release the non-nicotine pre-vapor formulation from the reservoir. As a result of the hermetic seal, the non-nicotine pre-vapor formulation may be isolated from the environment as well as the internal elements of the non-nicotine pod assembly 300 that may potentially react with the non-nicotine pre-vapor formulation, thereby reducing or preventing the possibility of adverse effects to the shelf-life and/or sensorial characteristics (e.g., flavor) of the non-nicotine pre-vapor formulation. The second housing section 308 may contain structures configured to activate the non-nicotine pod assembly 300 and to receive and heat the non-nicotine pre-vapor formulation released from the reservoir after the activation.

The non-nicotine pod assembly 300 may be activated manually by an adult vaper prior to the insertion of the non-nicotine pod assembly 300 into the device body 100. Alternatively, the non-nicotine pod assembly 300 may be activated as part of the insertion of the non-nicotine pod assembly 300 into the device body 100. In an example embodiment, the second housing section 308 of the pod body includes a perforator configured to release the non-nicotine pre-vapor formulation from the reservoir during the activation of the non-nicotine pod assembly 300. The perforator may be in a form of a first activation pin 314a and a second activation pin 314b, which will be discussed in more detail herein.

To activate the non-nicotine pod assembly 300 manually, an adult vaper may press the first activation pin 314a and the second activation pin 314b inward (e.g., simultaneously or sequentially) prior to inserting the non-nicotine pod assembly 300 into the through hole 150 of the device body 100. For instance, the first activation pin 314a and the second activation pin 314b may be manually pressed until the ends thereof are substantially even with the upstream end face of the non-nicotine pod assembly 300. In an example embodiment, the inward movement of the first activation pin 314a and the second activation pin 314b causes a seal of the reservoir to be punctured or otherwise compromised so as to release the non-nicotine pre-vapor formulation therefrom.

Alternatively, to activate the non-nicotine pod assembly 300 as part of the insertion of the non-nicotine pod assembly 300 into the device body 100, the non-nicotine pod assembly 300 may be initially positioned such that the first activation pin 314a and the second activation pin 314b are in contact with the upstream sidewall of the through hole 150. The upstream end of the non-nicotine pod assembly 300 may then be urged toward the upstream sidewall of the through hole 150 such that the first activation pin 314a and the second activation pin 314b are pushed (e.g., simultaneously) into the second housing section 308 and, thus, transitioned from a protracted state to a retracted state to release the non-nicotine pre-vapor formulation from the reservoir. Once the pod electrical contacts of the non-nicotine pod assembly 300 are adjacent to or touching the device electrical contacts of the device body 100, the downstream end of the non-nicotine pod assembly 300 can be maneuvered (e.g., pivoted) into the through hole 150. As the non-nicotine pod assembly 300 progresses into the through hole 150, the upstream engagement panel 156 and/or the downstream engagement panel 158 will flex and then spring back once the recesses of the non-nicotine pod assembly 300 become engaged with the corresponding protrusions of the device body 100.

In an example embodiment, when the non-nicotine pod assembly 300 is seated within the device body 100, the first upstream recess 312a and the second upstream recess 312b of the non-nicotine pod assembly 300 will be engaged with the first upstream protrusion 128a and the second upstream protrusion 128b, respectively, of the bezel structure 112 (e.g., upstream engagement). Similarly, the first downstream recess 306a and the second downstream recess 306b of the non-nicotine pod assembly 300 will be engaged with the first downstream protrusion 130a and the second downstream protrusion 130b, respectively, of the bezel structure 112 (e.g., downstream engagement). The transition to the upstream and/or downstream engagements may produce an audible click and/or a haptic feedback to indicate that the non-nicotine pod assembly 300 is properly seated within the through hole 150 of the device body 100.

When properly seated, the non-nicotine pod assembly 300 will be connected to the device body 100 mechanically, electrically, and fluidically. Although the upstream engagement of the non-nicotine pod assembly 300 may occur before the downstream engagement in some instances, it should be understood that, alternatively, the downstream engagement may occur before (or simultaneously with) the upstream engagement in other instances. The engagement of the non-nicotine pod assembly 300 with the device body 100 as well as other aspects of the non-nicotine e-vaping device 500 may also be as described in U.S. application Ser. No. 16/696,189 titled "Non-nicotine Pod Assemblies And Non-nicotine E-vaping Devices", filed concurrently herewith, and in U.S. application Ser. No. 16/695,515, titled "Non-nicotine Pod Assemblies And Non-nicotine E-vaping Devices", filed concurrently herewith, the entire contents of each of which are incorporated herein by reference.

Figure 16:
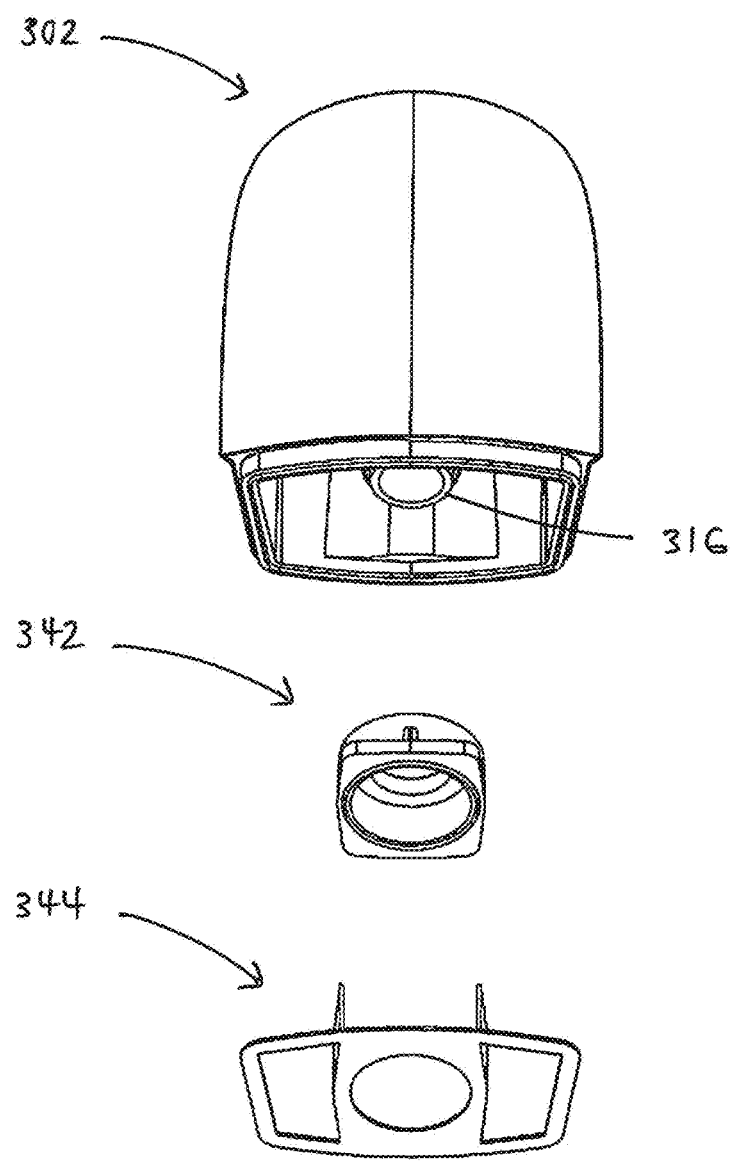
FIG. 16 is an exploded view involving the first housing section of the non-nicotine pod assembly of FIG. 14.

FIG. 16 is an exploded view involving the first housing section of the non-nicotine pod assembly of FIG. 14. Referring to FIG. 16, the first housing section 302 includes a vapor channel 316. The vapor channel 316 is configured to receive a non-nicotine vapor (from the second housing section 308) and is in fluidic communication with the pod outlet 304. In an example embodiment, the vapor channel 316 may gradually increase in size (e.g., diameter) as it extends towards the pod outlet 304. In addition, the vapor channel 316 may be integrally formed with the first housing section 302. An insert 342 and a seal 344 are disposed at an upstream end of the first housing section 302 to define the reservoir of the non-nicotine pod assembly 300. When assembled, the insert 342 may be resiliently interfaced with the outer sidewall of the vapor channel 316. Additionally, the seal 344 may be attached to the upstream rim of the first housing section 302 and the upstream side of the insert 342 to provide a fluid-tight (e.g., liquid-tight and/or air-tight) containment of the non-nicotine pre-vapor formulation in the reservoir.

Figure 17:
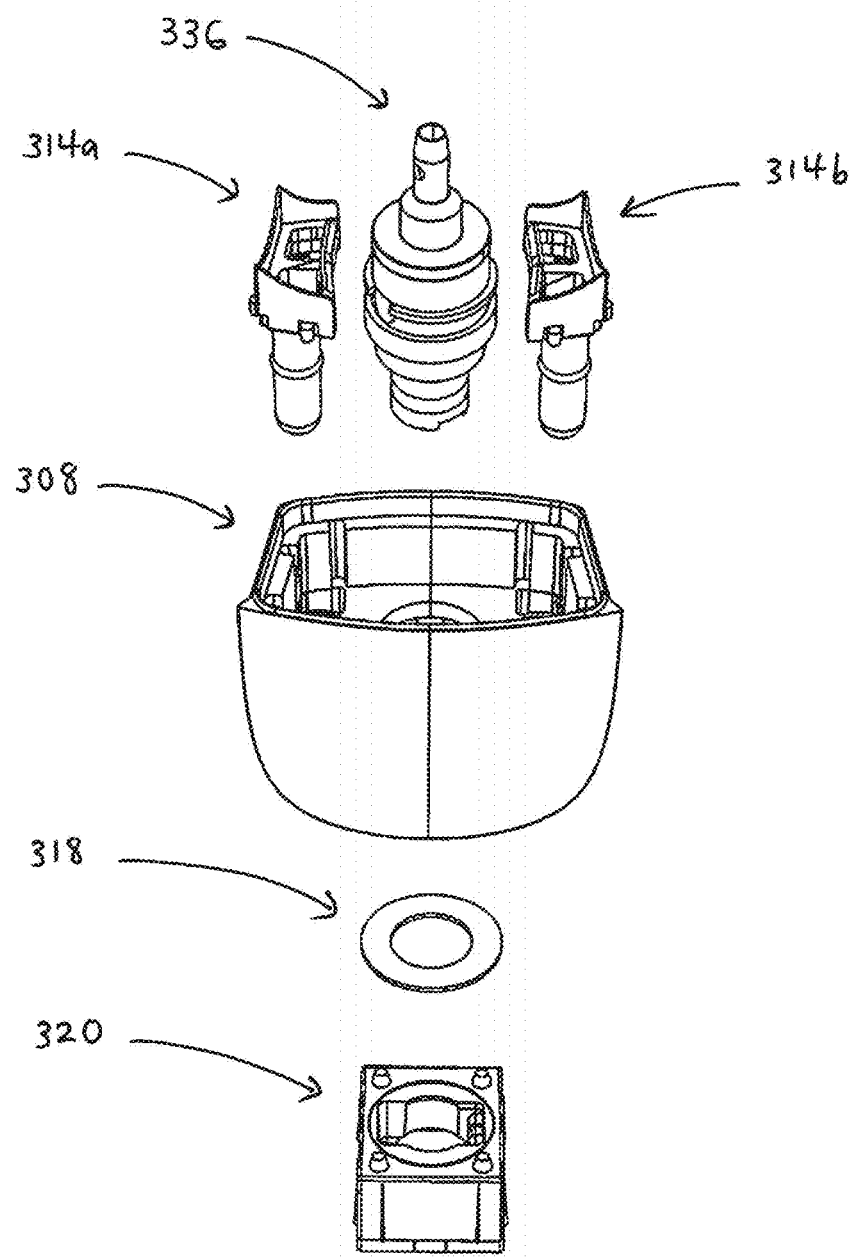
FIG. 17 is a partially exploded view involving the second housing section of the non-nicotine pod assembly of FIG. 14.

In an example embodiment, the seal 344 defines an opening (e.g., central opening) that is aligned with the vapor channel 316 and configured to provide the pertinent clearance to accommodate the downstream end of the vaporizer 336 (e.g., FIG. 17). In FIG. 16, it should be understood that the seal 344 is shown in a punctured state. In particular, when punctured by the first activation pin 314a and the second activation pin 314b of the non-nicotine pod assembly 300, the two punctured sections of the seal 344 will be pushed into the reservoir as flaps (as shown in FIG. 16), thus creating two punctured openings (e.g., one on each side of the central opening) in the seal 344. In contrast, when in an unpunctured state, the seal 344 will have a planar form and only one opening (e.g., central opening). The seal 344 is designed to be strong enough to remain intact during the normal movement and/or handling of the non-nicotine pod assembly 300 so as to avoid being prematurely/inadvertently breached. For instance, the seal 344 may be a coated foil (e.g., aluminum-backed polyethylene terephthalate (PET)).

FIG. 17 is a partially exploded view involving the second housing section of the non-nicotine pod assembly of FIG. 14. Referring to FIG. 17, the second housing section 308 is structured to contain various components configured to release, receive, and heat the non-nicotine pre-vapor formulation. For instance, the first activation pin 314a and the second activation pin 314b are configured to puncture the reservoir in the first housing section 302 to release the non-nicotine pre-vapor formulation. Each of the first activation pin 314a and the second activation pin 314b has a distal end that extends through corresponding openings in the second housing section 308. In an example embodiment, the distal ends of the first activation pin 314a and the second activation pin 314b are visible after assembly (e.g., FIG. 14), while the remainder of the first activation pin 314a and the second activation pin 314b are hidden from view within the non-nicotine pod assembly 300. In addition, each of the first activation pin 314a and the second activation pin 314b has a proximal end that is positioned so as to be adjacent to and upstream from the seal 344 prior to activation of the non-nicotine pod assembly 300. When the first activation pin 314a and the second activation pin 314b are pushed into the second housing section 308 to activate the non-nicotine pod assembly 300, the proximal end of each of the first activation pin 314a and the second activation pin 314b will advance and, as a result, puncture the seal 344, which will release the non-nicotine pre-vapor formulation from the reservoir. The movement of the first activation pin 314a may be independent of the movement of the second activation pin 314b (and vice versa). The first activation pin 314a and the second activation pin 314b will be discussed in more detail herein.

In an example embodiment, the rear surface of the second housing section 308 defines a pod inlet (e.g., FIG. 3). The pod inlet (through which air enters during vaping) is in fluidic communication with the pod outlet 304 (through which a non-nicotine vapor exits during vaping). The pod inlet may be located along a longitudinal axis of the non-nicotine pod assembly 300 (and the non-nicotine e-vaping device 500) and adjacent to the upstream end of the second housing section 308, although example embodiments are not limited thereto. Additionally, the pod inlet may be located between a pair of elevated surfaces (e.g., ridges) on the rear surface of the second housing section 308. As a result, the elevated surfaces may help reduce or prevent the blockage of the pod inlet (e.g., inadvertent blockage by the finger(s) of an adult vaper during vaping). The pod inlet is shown (e.g., FIG. 3) as being in a form of a slot. However, it should be understood that example embodiments are not limited thereto and that other forms are possible.

The upstream end of the second housing section 308 defines a cavity (e.g., underside of the second housing section 308 based on the view in FIG. 17). As noted supra, the cavity is configured to receive the connector module 320 (e.g., via interference fit). In an example embodiment, the cavity is situated between the first upstream recess 312a and the second upstream recess 312b and also situated between the first activation pin 314a and the second activation pin 314b. In the absence of the connector module 320, a gasket 318 and an upstream end of the vaporizer 336 (which extends through the gasket 318) may be visible via the cavity in the second housing section 308.

The vaporizer 336 is configured to receive and heat the non-nicotine pre-vapor formulation released from the reservoir in the first housing section 302. As will be discussed in more detail below, the vaporizer 336 may include a wick and/or a heater configured to receive and heat the non-nicotine pre-vapor formulation. In addition, the vaporizer 336 may be regarded as having an upstream end, an opposing downstream end, and an intermediate sector between the upstream end and the downstream end. The upstream end of the vaporizer 336 is configured to extend through the second housing section 308 and the gasket 318 to engage with the connector module 320. For instance, the upstream end of the vaporizer 336 may be seated within a corresponding socket in the connector module 320 (e.g., via an interference fit). On the other hand, the downstream end of the vaporizer 336 is configured to extend through the seal 344 and the insert 342 to engage with the vapor channel 316 of the first housing section 302. The intermediate sector of the vaporizer 336 defines an internal heating chamber along with one or more openings leading thereto that are configured to receive the non-nicotine pre-vapor formulation released from the reservoir in the first housing section 302 when the non-nicotine pod assembly 300 is activated.

In an example embodiment, the intermediate sector of the vaporizer 336 defines a pair of openings upstream from the seal 344. The vaporizer 336 may include a wick within and/or extending through both of the openings in the intermediate sector. The wick has pores/interstices designed for capillary action. In addition, a heater may be arranged within the heating chamber in the intermediate sector of the vaporizer 336 so as to be in thermal contact with the wick. As a result, the non-nicotine pre-vapor formulation released from the reservoir may be transported via the wick to the heater in the intermediate sector of the vaporizer 336. The heater is configured to heat the non-nicotine pre-vapor formulation during vaping to generate a non-nicotine vapor. The heater is electrically connected to at least one electrical contact of the connector module 320. For instance, one end (e.g., first end) of the heater may be connected to the first power contact 324a, while the other end (e.g., second end) of the heater may be connected to the second power contact 324b. The heater may include a coiled heating element. In such an instance, the wick may have a string-like form with the heater wrapped (e.g., in a helical manner) around at least a portion of its length. Alternatively, the heater may include a folded heating element. In such an instance, the wick may have a planar form (e.g., fibrous pad) configured to be held by the folded heating element. Although various forms are discussed above in connection with the heater and the wick, it should be understood that other configurations and combinations are possible.

The heater may be configured to undergo Joule heating (which is also known as ohmic/resistive heating) upon the application of an electric current thereto. Stated in more detail, the heater may be formed of one or more conductors (resistive materials) and configured to produce heat when an electric current passes therethrough. The electric current may be supplied from a power source (e.g., battery) within the device body 100 and conveyed to the heater via the first power contact 324a or via the second power contact 324b. During vaping, the non-nicotine vapor generated by the heater is drawn from the heating chamber in the intermediate sector of the vaporizer 336, through the downstream end of the vaporizer 336, through the vapor channel 316 of the first housing section 302, out the pod outlet 304 of the non-nicotine pod assembly 300, and through the vapor passage 136 of the mouthpiece 102 to the vapor outlet(s).

Suitable conductors (resistive materials) for the heater include an iron-based alloy (e.g., stainless steel) and/or a nickel-based alloy (e.g., nichrome). A wire formed of such materials may be wound to provide a heater with a coiled form. In another instance, the heater may be fabricated from a conductive sheet (e.g., metal, alloy) that is stamped to cut a winding pattern therefrom. The winding pattern may have curved segments alternately arranged with horizontal segments so as to allow the horizontal segments to zigzag back and forth while extending in parallel. In addition, a width of each of the horizontal segments of the winding pattern may be substantially equal to a spacing between adjacent horizontal segments of the winding pattern, although example embodiments are not limited thereto. To obtain a folded form for the heater, the winding pattern may be folded or bent over upon itself (e.g., to provide a U-shaped cross-section configured to receive and grip the wick). The heater and associated structures are discussed in more detail in U.S. application Ser. No. 15/729,909, titled "Folded Heater For Electronic Vaping Device", filed Oct. 11, 2017, the entire contents of which is incorporated herein by reference.

Figure 18:
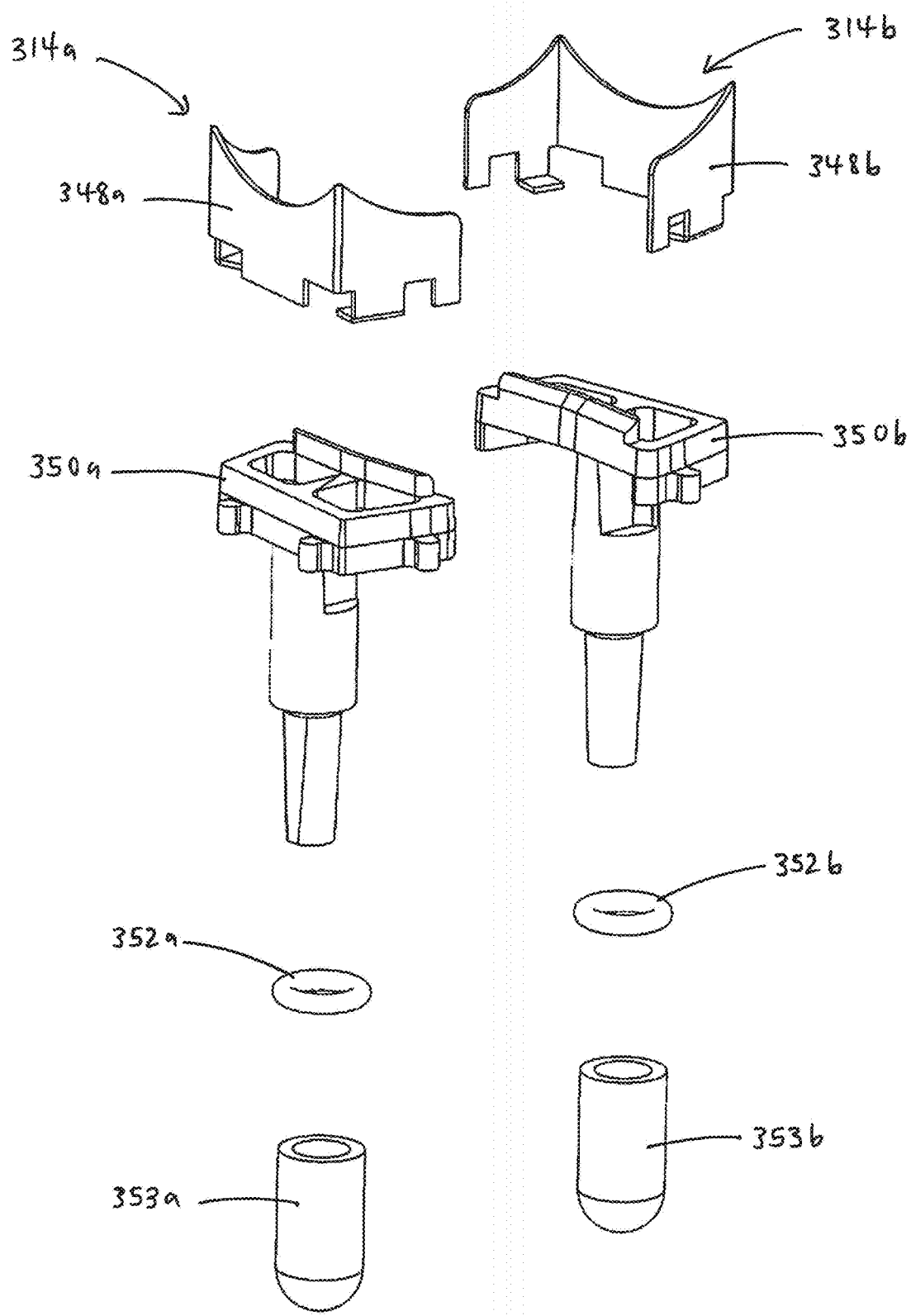
FIG. 18 is an exploded view of the activation pin in FIG. 17.

FIG. 18 is an exploded view of the activation pin in FIG. 17. Referring to FIG. 18, the activation pin may be in the form of a first activation pin 314a and a second activation pin 314b. While two activation pins are shown and discussed in connection with the non-limiting embodiments herein, it should be understood that, alternatively, the non-nicotine pod assembly 300 may include only one activation pin. In FIG. 18, the first activation pin 314a may include a first blade 348a, a first actuator 350a, a first O-ring 352a, and a first cap 353a. Similarly, the second activation pin 314b may include a second blade 348b, a second actuator 350b, a second O-ring 352b, and a second cap 353b.

In an example embodiment, the first blade 348a and the second blade 348b are configured to be mounted or attached to upper portions (e.g., proximal portions) of the first actuator 350a and the second actuator 350b, respectively. The mounting or attachment may be achieved via a snap-fit connection, an interference fit (e.g., friction fit) connection, an adhesive, or other suitable coupling technique. The top of each of the first blade 348a and the second blade 348b may have one or more curved or concave edges that taper upward to a pointed tip. For instance, each of the first blade 348a and the second blade 348b may have two pointed tips with a concave edge therebetween and a curved edge adjacent to each pointed tip. The radii of curvature of the concave edge and the curved edges may be the same, while their arc lengths may differ. The first blade 348a and the second blade 348b may be formed of a sheet metal (e.g., stainless steel) that is cut or otherwise shaped to have the desired profile and bent to its final form. In another instance, the first blade 348a and the second blade 348b may be formed of plastic.

Additionally, as shown in FIG. 18, the first actuator 350a and the second actuator 350b may include projecting edges (e.g., curved inner lips which face each other) configured to push the two punctured sections of the seal 344 into the reservoir as the first blade 348a and the second blade 348b advance into the reservoir. In a non-limiting embodiment, when the first activation pin 314a and the second activation pin 314b are fully inserted into the non-nicotine pod assembly 300, the two flaps (from the two punctured sections of the seal 344, as shown in FIG. 16) may be between the sidewalls of the insert 342 and the projecting edges of the first actuator 350a and the second actuator 350b. As a result, the likelihood of the two punctured openings in the seal 344 becoming obstructed (by the two flaps from the two punctured sections) may be reduced or prevented. Furthermore, the first actuator 350a and the second actuator 350b may be configured to guide the non-nicotine pre-vapor formulation from the reservoir toward the openings in the vaporizer 336 (which lead to the heating chamber within).

The lower portion (e.g., distal portion) of each of the first actuator 350a and the second actuator 350b is configured to extend through a bottom section (e.g., upstream end) of the second housing section 308. This rod-like portion of each of the first actuator 350a and the second actuator 350b may also be referred to as the shaft. The first O-ring 352a and the second O-ring 352b may be disposed on the respective shafts of the first actuator 350a and the second actuator 350b. In an example embodiment, the first cap 353a may be used to help secure the first O-ring 352a against a recessed surface of the shaft of the first actuator 350a. Similarly, the second cap 353b may be used to help secure the second O-ring 352b against a recessed surface of the shaft of the second actuator 350b.

The first O-ring 352a and the second O-ring 352b are configured to engage with the respective shafts of the first actuator 350a and the second actuator 350b as well as the inner surfaces of the corresponding openings in the second housing section 308 in order to provide a fluid-tight seal. As a result, when the first activation pin 314a and the second activation pin 314b are pushed inward to activate the non-nicotine pod assembly 300, the first O-ring 352a and the second O-ring 352b may move together with the respective shafts of the first actuator 350a and the second actuator 350b within the corresponding openings in the second housing section 308 while maintaining their respective seals, thereby helping to reduce or prevent leakage of the non-nicotine pre-vapor formulation through the openings in the second housing section 308 for the first activation pin 314a and the second activation pin 314b. The first O-ring 352a and the second O-ring 352b may be formed of silicone.

FIG. 19 is an exploded view of the connector module of FIG. 17. Referring to FIG. 19, the module housing 354 and the face plate 366 generally form the exterior framework of the connector module 320. In particular, the connector module 320 may be regarded as having a plurality of faces, including an external face and adjacent side faces. In an example embodiment, the external face of the connector module 320 includes the upstream surface of the face plate 366 (e.g., the underside of the face plate 366 based on the view in FIG. 19). The side faces of the connector module 320 may be part of the module housing 354. Although hidden from view, the rear side face of the module housing 354 may define a module inlet (e.g., the side face of the module housing 354 angled toward the back left based on the view in FIG. 19). The side faces may include rib structures (e.g., crush ribs) configured to facilitate an interference fit when the connector module 320 is seated within the cavity in the second housing section 308. For instance, each of the side faces may include a pair of rib structures that taper away from the face plate 366. As a result, the module housing 354 will encounter increasing resistance via the friction of the rib structures against the walls of the cavity as the connector module 320 is pressed into the cavity of the second housing section 308. When the connector module 320 is properly seated, the module inlet in the module housing 354 will be aligned with the pod inlet in the second housing section 308.

A sensor 364, first power contact 324a, second power contact 324b, and printed circuit board (PCB) 362 are disposed within the exterior framework formed by the module housing 354 and the face plate 366. In an example embodiment, the sensor 364 is configured to detect and/or measure a flow of air into the non-nicotine pod assembly 300. For instance, the sensor 364 may be a hot-wire anemometer that is positioned such that the wire portion extends across the module inlet in the module housing 354. The face plate 366 defines a plurality of contact openings. The data contacts 326 are configured to extend through the corresponding contact openings in the face plate 366 to electrically connect to the printed circuit board 362.

Each of the first power contact 324a and second power contact 324b may be regarded as having a body portion, an arm portion, a finger portion, and a leg portion. When assembled, the body portions of the first power contact 324a and second power contact 324b may be adjacent to the rear side face of the module housing 354 (e.g., the side face of the module housing 354 angled toward the back left based on the view in FIG. 19). Additionally, the arm portions of the first power contact 324a and second power contact 324b may be adjacent to the lateral side faces of the module housing 354 (e.g., the two side faces extending from the rear side face). The finger portions of the first power contact 324a and second power contact 324b may each be in the form of two fingers that will electrically connect to the heater in the vaporizer 336 (e.g., via electrical leads) when the upstream end of the vaporizer 336 is seated within the corresponding socket defined by the module housing 354 of the connector module 320. Once the face plate 366 is in place and engaged with the module housing 354, the leg portions of the first power contact 324a and second power contact 324b may be bent toward the finger portions such that the leg portions are adjacent to or against the upstream surface of the face plate 366 (e.g., the underside of the face plate 366 based on the view in FIG. 19). Thus, when assembled, the printed circuit board 362 may be regarded as being surrounded on at least four sides by the meandering structures of the first power contact 324a and the second power contact 324b.

The resistance-to-draw (RTD) for the non-nicotine e-vaping device 500 may be adjusted by changing the size of the module inlet (in the module housing 354) rather than changing the size of the pod inlet (in the second housing section 308). In an example embodiment, the size of the module inlet may be selected such that the resistance-to-draw is between 25-100 mmH$_2$O (e.g., between 30-50 mmH$_2$O). For instance, a diameter of 1.0 mm for the module inlet may result in a resistance-to-draw of 88.3 mmH$_2$O. In another instance, a diameter of 1.1 mm for the module inlet may result in a resistance-to-draw of 73.6 mmH$_2$O. In another instance, a diameter of 1.2 mm for the module inlet may result in a resistance-to-draw of 58.7 mmH$_2$O. In yet another instance, a diameter of 1.3 mm for the module inlet may result in a resistance-to-draw of about 40-43 mmH$_2$O.

In an example embodiment, the pod inlet in the second housing section 308 is larger than the module inlet in the module housing 354. In such an instance, the module inlet in the module housing 354 may be the limiting factor with regard the flow of air into the non-nicotine pod assembly 300. As a result, the size of the module inlet, because of its internal arrangement, may be adjusted without affecting the external aesthetics of the non-nicotine pod assembly 300, thereby allowing for a more standardized product design for non-nicotine pod assemblies with various resistance-to-draw (RTD) while also reducing the likelihood of an inadvertent blockage of the incoming air. The non-nicotine pod assembly 300 as well as other aspects of the non-nicotine e-vaping device 500 may also be as described in U.S. application Ser. No. 16/696,081, titled "Non-nicotine Pod Assemblies And Non-nicotine E-vaping Devices", filed concurrently herewith, the entire contents of which is incorporated herein by reference.

In an example embodiment, the non-nicotine pre-vapor formulation neither includes tobacco nor is derived from tobacco. A non-nicotine compound of the non-nicotine pre-vapor formulation may be part of, or included in a liquid or a partial-liquid that includes an extract, an oil, an alcohol, a tincture, a suspension, a dispersion, a colloid, a general non-neutral (slightly acidic or slightly basic) solution, or combinations thereof. During the preparation of the non-nicotine pre-vapor formulation, the non-nicotine compound may be infused into, comingled, or otherwise combined with the other ingredients of the non-nicotine pre-vapor formulation.

In an example embodiment, the non-nicotine compound undergoes a slow, natural decarboxylation process over an extended duration of time at relatively low temperatures, including at or below room temperature (e.g., 72° F.). In addition, the non-nicotine compound may undergo a significantly elevated decarboxylation process (e.g., 50% decarboxylation or greater) if exposed to elevated temperatures, especially in the range of about 175° F. or greater over a period of time (minutes or hours) at a relatively low pressure such as 1 atmosphere. Higher temperatures of about 240° F. or greater can cause a rapid or instantaneous decarboxylation to occur at a relatively high decarboxylation rate, although further elevated temperatures can cause a degradation of some or all of the chemical properties of the non-nicotine compound(s).

In an example embodiment, the non-nicotine compound may be from a medicinal plant (e.g., a naturally-occurring constituent of a plant that provides a medically-accepted therapeutic effect). The medicinal plant may be a *cannabis* plant, and the constituent may be at least one *cannabis*-derived constituent. Cannabinoids (e.g., phytocannabinoids) and terpenes are examples of *cannabis*-derived constituents. Cannabinoids interact with receptors in the body to produce a wide range of effects. As a result, cannabinoids have been used for a variety of medicinal purposes. *Cannabis*-derived materials may include the leaf and/or flower material from one or more species of *cannabis* plants, or extracts from the one or more species of *cannabis* plants. For instance, the one or more species of *cannabis* plants may include *Cannabis sativa, Cannabis indica*, and *Cannabis ruderalis*. In some example embodiments, the non-nicotine pre-vapor formulation includes a mixture of *cannabis* and/or *cannabis*-derived constituents that are, or are derived from, 60-80% (e.g., 70%) *Cannabis sativa* and 20-40% (e.g., 30%) *Cannabis indica*.

Non-limiting examples of *cannabis*-derived cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid. (CBDA) may be converted to tetrahydrocannabinol (THC) and cannabidiol (CBD), respectively, via heating. In an example embodiment, heat from the heater may cause decarboxylation to convert tetrahydrocannabinolic acid (THCA) in the non-nicotine pre-vapor formulation to tetrahydrocannabinol (THC), and/or to convert cannabidiolic acid (CBDA) in the non-nicotine pre-vapor formulation to cannabidiol (CBD).

In instances where both tetrahydrocannabinolic acid (THCA) and tetrahydrocannabinol (THC) are present in the non-nicotine pre-vapor formulation, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC), via the decarboxylation process, during the heating of the non-nicotine pre-vapor formulation for purposes of vaporization. Similarly, in instances where both cannabidiolic acid (CBDA) and cannabidiol (CBD) are present in the non-nicotine pre-vapor formulation, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD), via the decarboxylation process, during the heating of the non-nicotine pre-vapor formulation for purposes of vaporization.

The non-nicotine pre-vapor formulation may contain the non-nicotine compound that provides the medically-accepted therapeutic effect (e.g., treatment of pain, nausea, epilepsy, psychiatric disorders). Details on methods of treatment may be found in U.S. application Ser. No. 15/845,501, filed Dec. 18, 2017, titled "VAPORIZING DEVICES AND METHODS FOR DELIVERING A COMPOUND USING THE SAME," the disclosure of which is incorporated herein in its entirety by reference.

In an example embodiment, at least one flavorant is present in an amount ranging from about 0.2% to about 15% by weight (e.g., about 1% to 12%, about 2% to 10%, or about 5% to 8%) based on a total weight of the non-nicotine pre-vapor formulation. The at least one flavorant may be at least one of a natural flavorant, an artificial flavorant, or a combination of a natural flavorant and an artificial flavorant. The at least one flavorant may include volatile *cannabis* flavor compounds (flavonoids) or other flavor compounds instead of, or in addition to, the *cannabis* flavor compounds. For instance, the at least one flavorant may include menthol, wintergreen, peppermint, cinnamon, clove, combinations thereof, and/or extracts thereof. In addition, flavorants may be included to provide other herb flavors, fruit flavors, nut flavors, liquor flavors, roasted flavors, minty flavors, savory flavors, combinations thereof, and any other desired flavors.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A non-nicotine e-vaping device, comprising:
a non-nicotine pod assembly configured to hold a non-nicotine pre-vapor formulation, the non-nicotine pod assembly having an upstream end and a downstream end, the upstream end defining at least one upstream recess, the downstream end defining at least one downstream recess; and
a device body defining a through hole configured to receive the non-nicotine pod assembly, the through hole including an upstream sidewall and a downstream sidewall, at least one of the upstream sidewall or the downstream sidewall configured to deflect during an insertion of the non-nicotine pod assembly, the upstream sidewall including at least one upstream protrusion, the downstream sidewall including at least one downstream protrusion, the at least one upstream protrusion and the at least one downstream protrusion configured to engage with the at least one upstream recess and the at least one downstream recess, respectively, so as to retain the non-nicotine pod assembly within the through hole of the device body.

2. The non-nicotine e-vaping device of claim 1, wherein the upstream sidewall and the downstream sidewall of the device body are configured to flex away from each other during the insertion of the non-nicotine pod assembly.

3. The non-nicotine e-vaping device of claim 1, wherein the upstream sidewall and the downstream sidewall of the device body are resilient sections configured to transition from an unloaded state to a loaded state when the non-nicotine pod assembly is received by the device body.

4. The non-nicotine e-vaping device of claim 3, wherein the at least one upstream protrusion is urged by the upstream sidewall of the device body to interlock with the at least one upstream recess of the non-nicotine pod assembly during the loaded state.

5. The non-nicotine e-vaping device of claim 3, wherein the at least one downstream protrusion is urged by the downstream sidewall of the device body to interlock with the at least one downstream recess of the non-nicotine pod assembly during the loaded state.

6. The non-nicotine e-vaping device of claim 1, wherein the device body includes a bezel structure defining the through hole.

7. The non-nicotine e-vaping device of claim 6, wherein the bezel structure is a monolithic article.

8. The non-nicotine e-vaping device of claim 6, wherein the bezel structure includes a first upstream corner defining a first upstream slit, a second upstream corner defining a second upstream slit, a first downstream corner defining a first downstream slit, and a second downstream corner defining a second downstream slit.

9. The non-nicotine e-vaping device of claim 8, wherein the upstream sidewall is between the first upstream slit and the second upstream slit, and the downstream sidewall is between the first downstream slit and the second downstream slit.

10. The non-nicotine e-vaping device of claim 8, wherein the bezel structure has a length, a width, and a depth, the width being greater than the depth.

11. The non-nicotine e-vaping device of claim 10, wherein each of the first upstream slit, the second upstream slit, the first downstream slit, and the second downstream slit has a longest dimension that is at least 30 percent of the depth of the bezel structure.

12. The non-nicotine e-vaping device of claim 6, wherein the device body further includes a mouthpiece secured to the bezel structure.

13. The non-nicotine e-vaping device of claim 12, wherein the mouthpiece includes a male portion, the bezel structure includes a female portion, and the male portion of the mouthpiece and the female portion of the bezel structure are configured to mate as a bayonet connection.

14. The non-nicotine e-vaping device of claim 1, wherein the at least one upstream recess and the at least one downstream recess of the non-nicotine pod assembly are in a form of a dimple.

15. The non-nicotine e-vaping device of claim 1, wherein the at least one upstream recess of the non-nicotine pod assembly includes two upstream recesses, and the at least one downstream recess of the non-nicotine pod assembly includes two downstream recesses.

16. The non-nicotine e-vaping device of claim 1, wherein the at least one upstream protrusion and the at least one downstream protrusion of the device body are in a form of a spherical cap.

17. The non-nicotine e-vaping device of claim 1, wherein the at least one upstream protrusion of the device body includes two upstream protrusions, and the at least one downstream protrusion of the device body includes two downstream protrusions.

18. The non-nicotine e-vaping device of claim 1, wherein the device body is configured to produce at least one of an audible click or a haptic feedback in response to the non-nicotine pod assembly being seated within the through hole of the device body.

19. A device body for a non-nicotine e-vaping device, comprising:
a device housing defining a through hole configured to receive a non-nicotine pod assembly, the through hole including an upstream sidewall and a downstream sidewall, at least one of the upstream sidewall or the downstream sidewall configured to deflect during an insertion of the non-nicotine pod assembly, the upstream sidewall including at least one upstream protrusion, the downstream sidewall including at least one downstream protrusion, the at least one upstream protrusion and the at least one downstream protrusion configured to engage with at least one upstream recess and at least one downstream recess, respectively, of the non-nicotine pod assembly so as to retain the non-nicotine pod assembly within the through hole.

20. A non-nicotine pod assembly for a non-nicotine e-vaping device, comprising:
a pod body configured to hold a non-nicotine pre-vapor formulation, the pod body having a front face, a rear face, a first side face, a second side face, an upstream end, and a downstream end, the upstream end including at least one electrical contact and defining at least one upstream recess, the at least one electrical contact being on an outer surface of the upstream end, the downstream end defining a pod outlet and at least one downstream recess.

21. The non-nicotine pod assembly of claim 20, wherein the at least one upstream recess includes two upstream recesses, the at least one electrical contact being between the two upstream recesses, the at least one downstream recess includes two downstream recesses, the pod outlet being between the two downstream recesses.

22. The non-nicotine pod assembly of claim 20, wherein the at least one electrical contact includes a planar surface.

23. The non-nicotine pod assembly of claim 20, wherein the at least one downstream recess is adjacent to the pod outlet.

* * * * *